United States Patent
Walters et al.

(10) Patent No.: US 12,076,511 B2
(45) Date of Patent: Sep. 3, 2024

(54) INTRA-AORTIC BALLOON PUMP CATHETER AND SHEATH SEAL ASSEMBLY

(71) Applicant: DATASCOPE CORP., Wayne, NJ (US)

(72) Inventors: Daniel A. Walters, Rockaway Township, NJ (US); Gary Victor Schwarz, Midland Park, NJ (US); Matthew Hain, Wayne, NJ (US); Vito S. Savino, Ringwood, NJ (US); Igor Inga, Jr., Wayne, NJ (US)

(73) Assignee: DATASCOPE CORP., Wayne, NJ (US)

( * ) Notice: Subject to any disclaimer, the term of this patent is extended or adjusted under 35 U.S.C. 154(b) by 638 days.

(21) Appl. No.: 16/899,279

(22) Filed: Jun. 11, 2020

(65) Prior Publication Data

US 2020/0391014 A1   Dec. 17, 2020

Related U.S. Application Data

(60) Provisional application No. 62/862,544, filed on Jun. 17, 2019, provisional application No. 62/861,465, filed on Jun. 14, 2019.

(51) Int. Cl.
*A61M 25/10* (2013.01)
*A61M 25/02* (2006.01)

(52) U.S. Cl.
CPC . *A61M 25/1025* (2013.01); *A61M 2025/0293* (2013.01); *A61M 2025/1056* (2013.01);
(Continued)

(58) Field of Classification Search
CPC ........ A61M 25/1025; A61M 2210/125; A61M 2210/127; A61M 2025/0293
See application file for complete search history.

(56) References Cited

U.S. PATENT DOCUMENTS

| 3,585,983 A | 6/1971 | Kantrowitz et al. |
| 4,014,317 A | 3/1977 | Bruno |

(Continued)

FOREIGN PATENT DOCUMENTS

| DE | 198 26 746 C1 | 11/1999 |
| EP | 0611582 A2 | 8/1994 |

(Continued)

OTHER PUBLICATIONS

T.A. M. Chuter et al.; A Telescopic Stent-graft for Aortoiliac Implantation; European Journal of Vascular and Endovascular Surgery, Jan. 1997; pp. 79-84; vol. 13, Issue 1.
(Continued)

*Primary Examiner* — Bradley J Osinski

(57) ABSTRACT

Provided herein is an intra-aortic balloon catheter including a tube; and a sheath seal including an elastomeric housing having a proximal end, a distal end, a lumen arranged between the proximal end of the housing and the distal end of the housing, wherein the housing includes an impingement device, wherein the lumen is configured to slidably receive the tube therein and the impingement device is configured to engage the outer surface of the tube and apply a force thereto in order to prevent the tube from sliding relative to the sheath seal when the impingement device is in a first state.

29 Claims, 16 Drawing Sheets

(52) U.S. Cl.
CPC ............... *A61M 2025/1061* (2013.01); *A61M 2025/1081* (2013.01); *A61M 2205/3331* (2013.01); *A61M 2210/125* (2013.01); *A61M 2210/127* (2013.01); *A61M 2230/30* (2013.01)

(56) References Cited

U.S. PATENT DOCUMENTS

| | | | |
|---|---|---|---|
| 5,234,416 A * | 8/1993 | Macaulay | A61M 25/008 600/437 |
| 5,634,475 A | 6/1997 | Wolvek | |
| 5,733,260 A | 3/1998 | DeMaio et al. | |
| 5,928,132 A | 7/1999 | Leschinsky | |
| 6,013,069 A | 1/2000 | Sirhan et al. | |
| 6,024,693 A | 2/2000 | Schock et al. | |
| 6,136,025 A | 10/2000 | Barbut et al. | |
| 6,149,578 A | 11/2000 | Downey et al. | |
| 6,165,162 A | 12/2000 | Safar et al. | |
| 6,206,852 B1 | 3/2001 | Lee | |
| 6,210,319 B1 | 4/2001 | Williams et al. | |
| 6,213,975 B1 | 4/2001 | Laksin | |
| 6,238,382 B1 | 5/2001 | Schock et al. | |
| 6,346,092 B1 | 2/2002 | Leschinsky | |
| 6,497,678 B2 | 12/2002 | Schock | |
| 6,540,721 B1 | 4/2003 | Voyles et al. | |
| 6,602,270 B2 | 8/2003 | Leschinsky et al. | |
| 6,613,014 B1 | 9/2003 | Chi | |
| 6,616,597 B2 | 9/2003 | Schock et al. | |
| 6,635,046 B1 | 10/2003 | Barbut | |
| 6,746,431 B2 | 6/2004 | Pfeiffer et al. | |
| 6,830,559 B2 * | 12/2004 | Schock | A61M 60/841 604/915 |
| 6,935,999 B2 | 8/2005 | Schock et al. | |
| 7,112,170 B2 | 9/2006 | Schock et al. | |
| 7,229,403 B2 | 6/2007 | Schock et al. | |
| 7,927,268 B1 | 4/2011 | St. Germain et al. | |
| 8,066,628 B1 | 11/2011 | Jeevanandam et al. | |
| 8,323,174 B2 | 12/2012 | Jeevanandam et al. | |
| 8,444,625 B2 | 5/2013 | Stalker et al. | |
| 8,608,637 B2 | 12/2013 | Jeevanandam et al. | |
| 8,684,905 B2 | 4/2014 | Jeevanandam et al. | |
| 9,327,101 B2 | 5/2016 | Gianotti et al. | |
| 9,592,369 B2 | 3/2017 | Yamaguchi | |
| 9,770,574 B2 * | 9/2017 | McArthur | A61M 25/01 |
| 2004/0002678 A1 * | 1/2004 | Chi | A61M 25/0097 604/93.01 |
| 2010/0114063 A1 | 5/2010 | Recinella et al. | |
| 2016/0250444 A1 * | 9/2016 | Lampropoulos | A61M 25/0108 600/486 |
| 2016/0256304 A1 | 9/2016 | Roeder et al. | |
| 2017/0273628 A1 | 9/2017 | Ofek et al. | |
| 2017/0348049 A1 | 12/2017 | Vrba et al. | |
| 2018/0318564 A1 * | 11/2018 | Pigott | A61M 25/10184 |
| 2019/0015630 A1 | 1/2019 | Curtis | |

FOREIGN PATENT DOCUMENTS

| | | | |
|---|---|---|---|
| JP | 11023396 A * | 1/1999 | |
| JP | 2000193546 A | 7/2000 | |
| JP | 2007260312 A | 10/2007 | |
| JP | 2016 029983 A | 3/2016 | |
| WO | 2001/002045 A1 | 1/2001 | |

OTHER PUBLICATIONS

International Search Report and Written Opinion for International Application No. PCT/US2020/037315, dated Oct. 30, 2020.

* cited by examiner

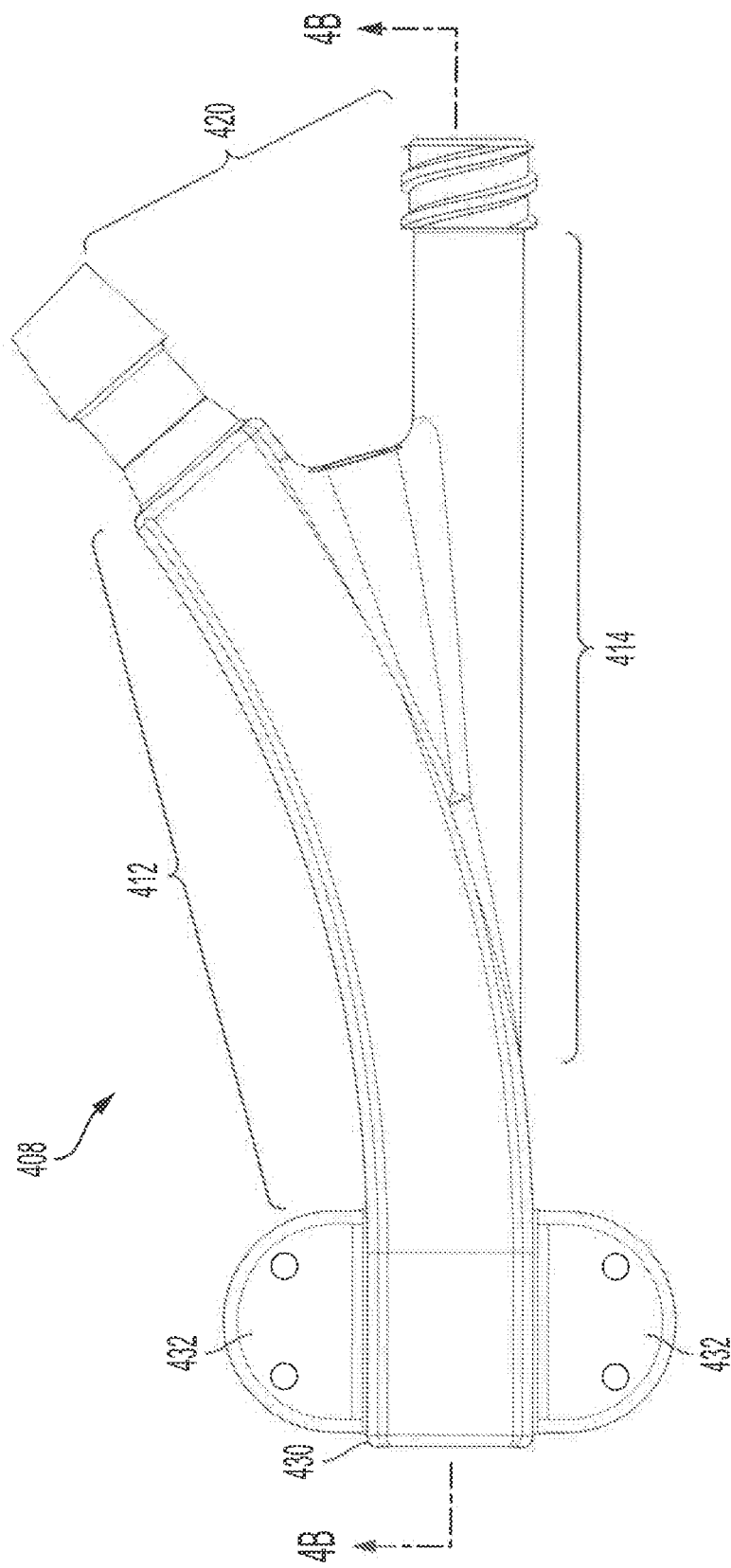

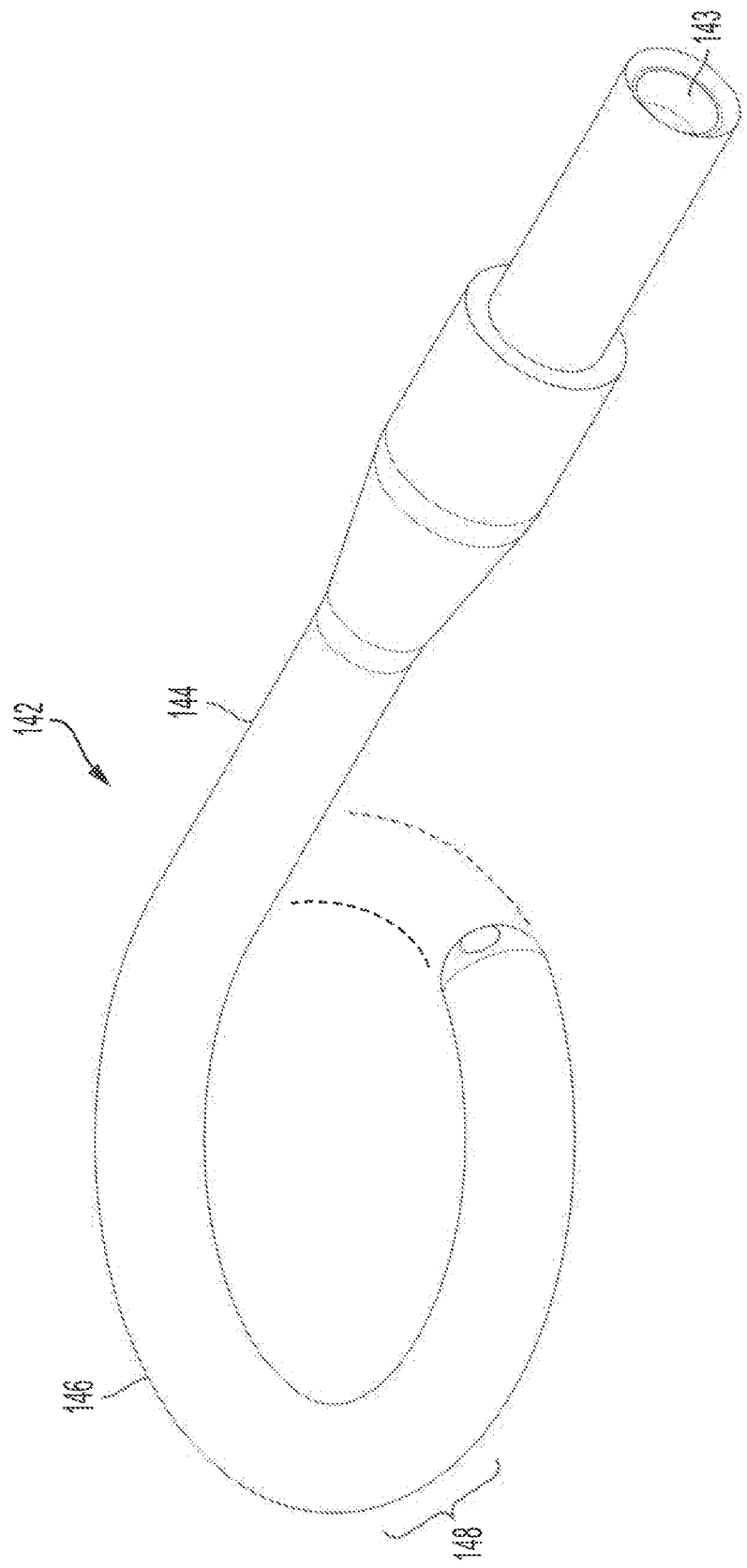

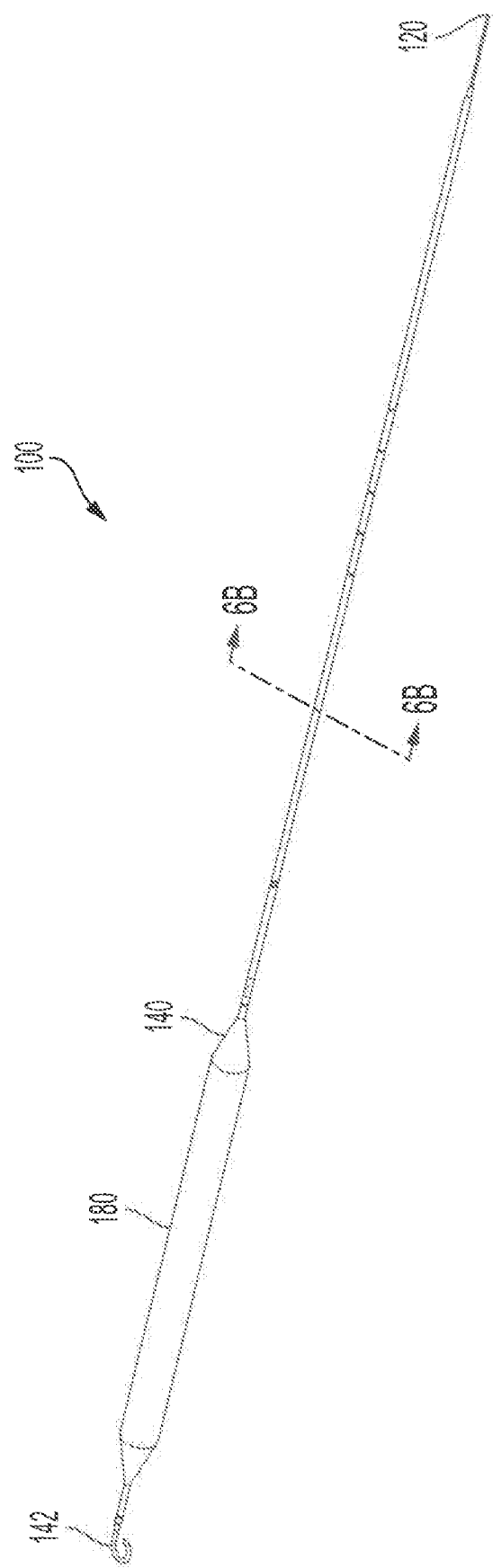

INTRA-AORTIC BALLOON PUMP CATHETER AND SHEATH SEAL ASSEMBLY

This application claims priority to, and the benefit of, co-pending U.S. Provisional Patent Application No. 62/861,465, filed on Jun. 14, 2019, and co-pending U.S. Provisional Patent Application No. 62/862,544, filed on Jun. 17, 2019, and the disclosures of these provisional patent applications are hereby incorporated by reference in their entirety for all they disclose.

BACKGROUND OF THE DISCLOSURE

Field of the Disclosure

Provided herein are cardiovascular assist devices and methods of using the same, and, in one particular non-limiting embodiment, an intra-aortic balloon pump (IABP) catheter, an assembly including an IABP and a sheath seal, and methods of using the same to provide cardiovascular assist by delivering the IABP through an axillary or subclavian artery.

Description of Related Art

Intra-aortic balloon pump (IABP) catheters are typically used in patients with left heart failure, for example left ventricular failure, to increase coronary artery perfusion and decrease the workload of the heart, again, for example, the left ventricle. The general arrangement and configuration of IABPs has not changed substantially for a few years, and this traditional configuration includes shortcomings.

IABPs are often introduced through an insertion sheath, into the femoral artery and through the descending thoracic aorta until the distal tip of the balloon is positioned just below (distal to) the left subclavian artery. The balloon is then cyclically inflated and deflated to provide assistance to the heart. Drawbacks to inserting IABPs via the femoral artery include that the patient must remain mostly supine while the IABP is in place, and the patient has limited mobility. There is a need to insert IABPs via other arteries, such as the axillary artery or the subclavian artery, so a patient is not confined to a mostly supine position with limited mobility while an IABP is in place. Thus, there is a need in the art for different configurations of IABPs, to allow for insertion through different vessels, and to maintain the location of IABPs within the patient's vasculature once delivered to a site of treatment.

IABP assemblies have in the past included a protective sleeve, optionally with an insertion sheath. Sheath seals have been used in such assemblies as well, for locking the protective sleeve and/or the IABP in place during heart assist treatments. U.S. Pat. No. 6,537,254 discloses such a sheath seal. However, there is a need in the art for sheath seals that exhibit improved resistance to movement of the IABP during heart assist treatment, for example, such as may be encountered in ambulatory heart assist therapies, while allowing movement or repositioning of the IABP when such movement or repositioning is desired by a physician or technician.

SUMMARY OF THE INVENTION

Accordingly, provided herein is a balloon catheter assembly including an intra-aortic balloon catheter comprising a proximal end, a distal end, and a tube arranged between the proximal end and the distal end, wherein the tube has an outer surface and an inner surface defining at least one lumen extending between the proximal end and the distal end, and a balloon membrane is disposed at the distal end, and a sheath seal comprising an elastomeric housing having a proximal end, a distal end, a lumen arranged between the proximal end of the housing and the distal end of the housing, wherein the housing comprises an impingement device, wherein the lumen is configured to slidably receive the tube therein and the impingement device is configured to engage the outer surface of the tube and apply a force thereto in order to prevent the tube from sliding relative to the sheath seal when the impingement device is in a first state.

Also provided herein is an intra-aortic balloon catheter having a proximal end, a distal end comprising a j-tip, a tube arranged between the proximal end and the distal end, the tube having an outer surface and an inner surface defining one or more lumens, and a balloon membrane disposed at the distal end.

Also provided herein is an intra-aortic balloon catheter having a proximal end, a distal end, a tube comprising a sidewall arranged between the proximal end and the distal end, wherein the sidewall has an outer surface and an inner surface defining a gas lumen, a sensor lumen in a co-lumen arrangement with the gas lumen, and a guidewire lumen in a co-lumen arrangement with the gas lumen and sharing a common wall with the sensor lumen, a balloon membrane disposed at the distal end and in fluid communication with the gas lumen.

Also provided herein is a method of intravascular balloon pumping of blood, including the steps of inserting, into a patient's axillary or subclavian artery, a balloon catheter assembly including an intra-aortic balloon catheter having a proximal end, a distal end, and a tube arranged between the proximal end and the distal end, wherein the tube has an outer surface and an inner surface defining at least one lumen extending between the proximal end and the distal end, and a balloon membrane disposed at the distal end and in fluid communication with the at least one lumen, and a sheath seal comprising an elastomeric housing comprising a proximal end, a distal end, a lumen arranged between the proximal end of the housing and the distal end of the housing, wherein the housing comprises an impingement device, wherein the lumen is configured to slidably receive the tube therein and the impingement device is configured to engage the outer surface of the tube and apply a force thereto, advancing the distal end of the balloon catheter to the patient's aorta, inflating and deflating the balloon membrane by passing a fluid into and out of the balloon membrane through the at least one lumen, thereby providing intravascular balloon pumping of blood.

Further non-limiting embodiments or aspects are set forth in the following numbered clauses:

Clause 1. A balloon catheter assembly comprising: an intra-aortic balloon catheter comprising a proximal end, a distal end, and a tube arranged between the proximal end and the distal end, wherein the tube has an outer surface and an inner surface defining at least one lumen extending between the proximal end and the distal end, and a balloon membrane is disposed at the distal end; and a sheath seal comprising an elastomeric housing comprising a proximal end, a distal end, a lumen arranged between the proximal end of the housing and the distal end of the housing, wherein the housing comprises an impingement device, wherein the lumen is configured to slidably receive the tube therein and the impingement device is configured to engage the outer surface of the tube and apply a force thereto in order to prevent the tube from sliding relative to the sheath seal when the impingement device is in a first state.

Clause 2. The balloon catheter assembly of clause 1, wherein the impingement device comprises a moveable pressure element disposed to exert pressure on the outer surface of the tube when the impingement device is in the first state in order to prevent the tube from sliding relative to the sheath seal, and wherein the pressure element is moveable to exert less pressure on the outer surface of the tube when the impingement device is in a second state so as to permit sliding of the tube relative to the sheath seal.

Clause 3. The balloon catheter assembly of clause 1 or clause 2, wherein the housing of the sheath seal further comprises a collapsible section arranged between the proximal end of the housing and the distal end of the housing, wherein the collapsible section is configured so that application of pressure to the collapsible section of the housing causes the impingement device to move from the first state to the second state.

Clause 4. The balloon catheter assembly of any of clauses 1-3, wherein the moveable pressure element is selected from the group consisting of a static interference pinch lock, a bend disposed in the housing, an off axis center section disposed to impinge the tube in the first state, and an offset pinch that opens the lumen of the housing when pinched.

Clause 5. The balloon catheter assembly of any of clauses 1-4, wherein the distal end of the housing of the sheath seal is tapered.

Clause 6. The balloon catheter assembly of any of clauses 1-5, wherein the housing of the sheath seal further comprises one or more suture pads configured to permit passage of a suture therethrough to allow the sheath seal to be secured to a patient.

Clause 7. The balloon catheter assembly of any of clauses 1-6, wherein the elastomeric housing comprises a thermoplastic elastomer.

Clause 8. The balloon catheter assembly of any of clauses 1-7, further comprising: a y-connection, comprising a hub having a proximal end, a distal end, and a lumen arranged between the proximal end and the distal end of the hub.

Clause 9. The balloon catheter assembly of any of clauses 1-8, wherein the y-connection hub is connected to the housing of the sheath seal.

Clause 10. The balloon catheter assembly of any of clauses 1-9, wherein between the proximal end of the y-connection hub and the distal end of the housing of the sheath seal there extends a lumen that is angled with respect to one or both of the lumen of the sheath seal and the lumen of the hub of the y-connection.

Clause 11. The balloon catheter assembly of any of clauses 1-10, wherein the impingement device comprises a channel defined by one or more sidewalls disposed in the lumen of the sheath seal.

Clause 12. The balloon catheter assembly of any of clauses 1-11, wherein a longitudinal axis defined by a center of the channel is offset from a longitudinal axis defined by a center of the lumen of the sheath seal.

Clause 13. The balloon catheter assembly of any of clauses 1-12, wherein the housing of the sheath seal comprises a plurality of tabs extending therefrom, and wherein application of pressure to the plurality of tabs moves the pressure element so the impingement device transitions to the second state.

Clause 14. The balloon catheter assembly of any of clauses 1-13, wherein the distal end of the balloon catheter comprises a pre-formed curved portion.

Clause 15. The balloon catheter assembly of any of clauses 1-14, wherein the pre-formed curved portion comprises a j-tip or a pigtail.

Clause 16. The balloon catheter assembly of any of clauses 1-15, wherein the j-tip comprises a first substantially straight segment connected to the distal end of the balloon catheter, a curved segment connected at a first end thereof to a distal end of the first substantially straight segment, and a second substantially straight segment attached to a second end of the curved segment, the second substantially straight segment arranged substantially parallel to the first substantially straight segment.

Clause 17. The balloon catheter assembly of any of clauses 1-16, wherein the j-tip comprises a thermoplastic.

Clause 18. The balloon catheter assembly of any of clauses 1-17, wherein the thermoplastic comprises a thermoplastic polyurethane.

Clause 19. The balloon catheter assembly of any of clauses 1-18, wherein the thermoplastic comprises a polyether-based thermoplastic polyurethane.

Clause 20. The balloon catheter assembly of any of clauses 1-19, wherein the j-tip comprises a metal.

Clause 21. The balloon catheter assembly of any of clauses 1-20, wherein a diameter of a theoretical circle formed by the j-tip and the balloon catheter is greater than 8 mm.

Clause 22. The balloon catheter assembly of any of clauses 1-21, wherein the distal end of the balloon catheter comprises an elongated extension.

Clause 23. The balloon catheter assembly of any of clauses 1-22, wherein the at least one lumen of the tube comprises a sensor lumen, a gas lumen, and a guidewire lumen.

Clause 24. The balloon catheter assembly of any of clauses 1-23, wherein the guidewire lumen is defined by a guidewire lumen sidewall comprising a polyimide tube.

Clause 25. The balloon catheter assembly of any of clauses 1-24, wherein the polyimide tube is embedded in a sidewall of the balloon catheter, and the polyimide tube and the gas lumen are arranged in a co-lumen arrangement.

Clause 26. The balloon catheter assembly of any of clauses 1-25, wherein the sensor lumen is defined by a sensor lumen sidewall and is arranged in a co-lumen arrangement with the gas lumen, and wherein the sensor lumen sidewall comprises one or more apertures in communication with an exterior of the balloon catheter.

Clause 27. The balloon catheter assembly of any of clauses 1-26, wherein the guidewire lumen and the sensor lumen share a common sidewall.

Clause 28. The balloon catheter assembly of any of clauses 1-27, further comprising a sensor disposed in the sensor lumen, wherein the sensor is disposed in a gap in the sensor lumen between two segments of a cured adhesive.

Clause 29. The balloon catheter assembly of any of clauses 1-28, wherein the sensor comprises a sensing portion embedded in a silicone gel.

Clause 30. The balloon catheter assembly of any of clauses 1-29, wherein the sensor is disposed at the distal end of the balloon catheter, proximal of the balloon membrane.

Clause 31. The balloon catheter assembly of any of clauses 1-30, wherein the sensor lumen, the gas lumen, and the guidewire lumen each have a cross-sectional diameter, and wherein the cross-sectional diameter of at least one of the sensor lumen, the gas lumen, and the guidewire lumen varies along a length of the balloon catheter.

Clause 32. The balloon catheter assembly of any of clauses 1-31, wherein the balloon catheter has a length of approximately 18 inches or less.

Clause 33. An intra-aortic balloon catheter comprising: a proximal end; a distal end comprising a j-tip; a tube arranged between the proximal end and the distal end, the tube having an outer surface and an inner surface defining one or more lumens; and a balloon membrane disposed at the distal end.

Clause 34. The balloon catheter of clause 33, wherein the j-tip comprises a first substantially straight segment connected to the distal end of the balloon catheter, a curved segment connected at a first end thereof to a distal end of the first substantially straight segment, and a second substantially straight segment attached to a second end of the curved segment, wherein the second substantially straight segment is arranged substantially parallel to the first substantially straight segment.

Clause 35. The balloon catheter of clause 33 or clause 34, wherein the j-tip comprises a thermoplastic.

Clause 36. The balloon catheter of any of clauses 33-35, wherein the thermoplastic comprises a thermoplastic polyurethane.

Clause 37. The balloon catheter of any of clauses 33-36, wherein the thermoplastic comprises a polyether-based thermoplastic polyurethane.

Clause 38. The balloon catheter of any of clauses 33-37, wherein the j-tip comprises a metal.

Clause 39. The balloon catheter of any of clauses 33-38, wherein a diameter of a theoretical circle formed by the j-tip and the balloon catheter is greater than 8 mm.

Clause 40. The balloon catheter of any of clauses 33-39, further comprising a sheath seal comprising an elastomeric housing comprising a proximal end, a distal end, a lumen arranged between the proximal end of the housing and the distal end of the housing, wherein the housing comprises one or more impingement devices, wherein the lumen is configured to slidably receive the tube therein and the one or more impingement devices are configured to engage the outer surface of the tube and apply force thereto in order to prevent the tube from sliding with respect to the sheath seal when each impingement device is in a first state.

Clause 41. The balloon catheter of any of clauses 33-40, wherein the one or more lumens comprise a sensor lumen, a gas lumen, and a guidewire lumen.

Clause 42. The balloon catheter of any of clauses 33-41, wherein the guidewire lumen is defined by a guidewire lumen sidewall comprising a polyimide tube.

Clause 43. The balloon catheter of any of clauses 33-42, wherein the polyimide tube is embedded in a sidewall of the balloon catheter, and the polyimide tube and the gas lumen are arranged in a co-lumen configuration.

Clause 44. The balloon catheter of any of clauses 33-43, wherein the sensor lumen is defined by a sensor lumen sidewall and is arranged in a co-lumen arrangement with the gas lumen, and wherein the sensor lumen sidewall comprises one or more apertures in communication with an exterior of the balloon catheter.

Clause 45. The balloon catheter of any of clauses 33-44, wherein the guidewire lumen and the sensor lumen share a common sidewall.

Clause 46. The balloon catheter of any of clauses 33-45, further comprising a sensor disposed in the sensor lumen, wherein the sensor is disposed in a gap in the sensor lumen between two segments of a cured adhesive.

Clause 47. The balloon catheter of any of clauses 33-46, wherein the sensor comprises a sensing portion embedded in a silicone gel.

Clause 48. The balloon catheter of any of clauses 33-47, wherein the sensor is disposed at the distal end of the balloon catheter, proximal of the balloon membrane.

Clause 49. The balloon catheter of any of clauses 33-48, wherein the balloon catheter has a length of approximately 18 inches or less.

Clause 50. The balloon catheter of any of clauses 33-49, wherein the one or more impingement devices include a first impingement device and a second impingement device that is a substantially different impingement device than the first impingement device.

Clause 51. The balloon catheter of any of clauses 33-50, wherein the first impingement device is a variable impingement device and the second impingement device is a static impingement device.

Clause 52. The balloon catheter of any of clauses 33-51, wherein the first impingement device is a variable impingement device that is substantially different from the second impingement device, wherein the second impingement device is also a variable impingement device.

Clause 53. The balloon catheter of any of clauses 33-52, wherein the sensor lumen has a circular cross sectional area, the guidewire lumen has a circular cross sectional area that is larger than the circular cross sectional area of the sensor lumen, and the gas lumen has a non-circular cross section that is at least twice the area of the combined cross sectional areas of the sensor lumen and the guidewire lumen.

Clause 54. An intra-aortic balloon catheter comprising: a proximal end; a distal end; a tube comprising a sidewall arranged between the proximal end and the distal end, wherein the sidewall has an outer surface and an inner surface defining a gas lumen, a sensor lumen in a co-lumen arrangement with the gas lumen, and a guidewire lumen in a co-lumen arrangement with the gas lumen and sharing a common wall with the sensor lumen; and a balloon membrane disposed at the distal end and in fluid communication with the gas lumen.

Clause 55. The balloon catheter of clause 54, wherein the balloon catheter has a length of approximately 18 inches or less.

Clause 56. The balloon catheter of clause 54 or clause 55, wherein the balloon catheter has a length of between approximately 14 inches and 18 inches.

Clause 57. The balloon catheter of any of clauses 54-56, further comprising a J-tip attached at the distal end, wherein the J-tip comprises a lumen that is contiguous with the guidewire lumen so that a guidewire is insertable through both the lumen of the J-tip and the guidewire lumen at the same time.

Clause 58. A method of intravascular balloon pumping of blood, comprising the steps of: inserting, into a patient's axillary or subclavian artery, a balloon catheter assembly comprising an intra-aortic balloon catheter comprising a proximal end, a distal end, and a tube arranged between the proximal end and the distal end, wherein the tube has an outer surface and an inner surface defining at least one lumen extending between the proximal end and the distal end, and a balloon membrane disposed at the distal end and in fluid communication with the at least one lumen, and a sheath seal comprising an elastomeric housing comprising a proximal end, a distal end, a lumen arranged between the proximal end of the housing and the distal end of the housing, wherein the housing comprises an impingement device, wherein the lumen is configured to slidably receive the tube therein and the impingement device is configured to engage the outer surface of the tube and apply a force thereto; advancing the distal end of the balloon catheter to the patient's aorta; and inflating and deflating the balloon membrane by passing a fluid into and out of the balloon membrane through the at least one lumen, thereby providing intravascular balloon pumping of blood.

Clause 59. The method of clause 58, wherein the housing of the sheath seal further comprises one or more suture pads configured to permit passage of a suture therethrough to allow the sheath seal to be secured to a patient, and wherein the method further comprises the step of securing the sheath seal to the patient.

BRIEF DESCRIPTION OF THE DRAWINGS

FIG. 4A is a top view of a y-connection according to a non-limiting embodiment or aspect of the disclosure;

FIGS. 5A-5B are perspective views of a balloon catheter and j-tip of a balloon catheter according to non-limiting embodiments or aspects of the disclosure;

FIG. 6A is a perspective view of a balloon catheter according to a non-limiting embodiment or aspect of the disclosure;

DESCRIPTION OF THE DISCLOSURE

Figure 1:
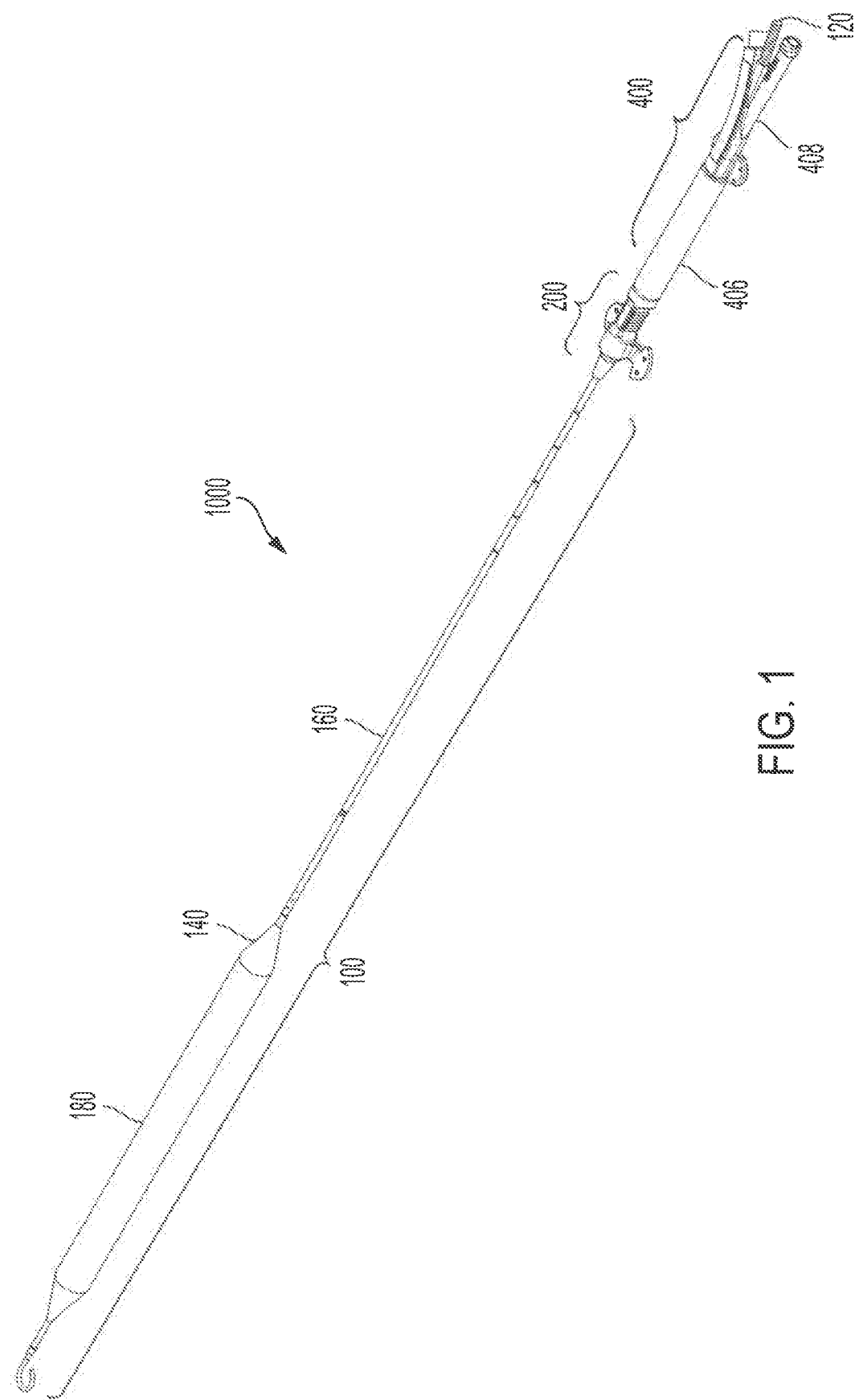
FIG. 1 is a perspective view of a balloon catheter assembly according to a non-limiting embodiment or aspect of the disclosure.

The following description is merely exemplary in nature and is in no way intended to limit or define an invention, its application, or uses. While the description is designed to permit one of ordinary skill in the art to make and use the subject matter disclosed, and specific examples are provided to that end, they should in no way be considered limiting. It will be apparent to one of ordinary skill in the art that various modifications to the following will fall within the scope of the appended claims. The present disclosure should not be considered limited to the presently disclosed aspects, whether provided in the examples or elsewhere herein.

For purposes of the description hereinafter, the terms "upper," "lower," "right," "left," "vertical," "horizontal," "top," "bottom," "lateral," "longitudinal," and derivatives thereof shall relate to the orientation shown in the drawing figures. However, it is to be understood that the systems and methods disclosed herein may assume various alternative variations and step sequences, except where expressly specified to the contrary. It is also to be understood that the specific devices and the method illustrated in the attached drawings, and described in the following specification, are simply exemplary embodiments. Hence, specific dimensions and other physical characteristics related to the embodiments disclosed herein are not to be considered as limiting.

The use of numerical values in the various ranges specified in this application, unless expressly indicated otherwise, are stated as approximations as though the minimum and maximum values within the stated ranges are both preceded by the word "about". In this manner, slight variations above and below the stated ranges (e.g., ±10%, 9%, 8%, 7%, 6%, 5%, 4%, 3%, 2%, 1%, or 0.5%) can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "patient" or "subject" refers to members of the animal kingdom including but not limited to, human beings and "mammal" refers to all mammals including, but not limited, to human beings.

As used herein, the terms "comprising," "comprise" or "comprised," and variations thereof, are open ended and do not exclude the presence of other elements not identified. In contrast, the term "consisting of" and variations thereof is intended to be closed and excludes additional elements in anything but trace amounts.

Provided herein is a balloon catheter assembly for use in, for example and without limitation, heart-assist treatment. The heart-assist treatment can be left heart-assist treatment. With reference to FIG. 1, in non-limiting embodiments or aspects the assembly 1000 includes an intra-aortic balloon catheter (referred herein interchangeably as intra-aortic balloon catheter and intra-aortic balloon pump (IABP)) 100, the IABP 100 having a proximal end 120, a distal end 140, and a tube 160 arranged therebetween. The tube 160 has an outer surface and an inner surface defining at least one lumen therethrough. The IABP 100 further includes a balloon membrane 180 disposed at the distal end 140 thereof.

The IABP 100, including tube 160 and/or the balloon membrane 180, can be of any useful diameter and length for delivering heart-assist treatment. In non-limiting embodiments or aspects, the tube 160 has a diameter of 8 French, 7.5 French, or 7 French. In non-limiting embodiments or aspects, the IABP 100 is about 18 inches in length. In non-limiting embodiments or aspects, the IABP 100 is about 18 inches in length or less, such as, for example and without limitation, 17 inches, 16 inches, 15 inches, 14 inches, 13 inches, 12 inches, 11 inches, 10 inches, 9 inches, 8 inches, or 7 inches when measured from the distal end of suture pads 432 of y-connection 408 to the base (proximal-most end) of the balloon membrane 180, all subranges therebetween inclusive. In non-limiting embodiments or aspects, the IABP 100 is between 14 inches and 18 inches in length, all subranges therebetween inclusive. Those of skill in the art will appreciate that patient size and insertion position (e.g., right or left-sided axillary artery insertion) will be at least partially determinative of the proper length of the IABP 100, and that various lengths can be selected based at least in part thereon. As described below, in non-limiting embodiments or aspects, the catheter assembly is delivered to a site of treatment within a patient through routes other than the traditional femoral-aortic route, such as via the axillary artery or the subclavian artery. In non-limiting embodiments or aspects, the IABP 100 is configured for insertion via the axillary artery or the subclavian artery, but it is not suitable for insertion via the femoral artery. Accordingly, an advantage of IABPs as described herein is that the devices, e.g., the tube 160, can be of a shorter length than that of a typical IABP.

The IABP 100, including tube 160 and balloon membrane 180, can be formed of any suitable material known to those of skill in the art. For example, and without limitation, the balloon membrane 180 can be formed of biocompatible metals and/or polymers. As used herein, the term "biocompatible" means that the material, and any degradation products thereof, are substantially non-toxic to cells or organisms. As used herein, "non-toxic" means that the material is at least non-carcinogenic, non-thrombogenic, and/or non-immunogenic when maintained in a patient's body for the duration of treatment. In non-limiting embodiments or aspects, the materials (e.g., metals and/or polymers) are biostable. As used herein, "biostable" means that the material is substantially non-biodegradable when deployed in a patient for a typical duration of use of an IABP.

In some non-limiting embodiments or aspects, the IABP 100 includes a metal or other rigid frame and a balloon membrane 180 thereon, and the balloon membrane 180 is an elastomeric material. In non-limiting embodiments or aspects, no frame is included, and the IABP 100 includes an elastomeric balloon membrane 180. In non-limiting embodiments or aspects, the balloon membrane 180 is formed of a polyurethane (PU) polymer or a PU-based co-polymer. As is known in the art, PUs can be formed from isocyanates and polyols. In non-limiting embodiments or aspects, PUs are formed by forming a prepolymer, by reacting or capping a macrodiol (e.g., a polyether, polyester, polycarbonate, and/or polysiloxane) with a diisocyanate. Then the prepolymer can be reacted/coupled with a diol or diamine. Those of skill in the art will appreciate that the above are merely exemplary, and that various other PUs, and methods of making the same, are known. So long as the polymeric material, such as a PU, is elastomeric and biocompatible, those of skill in the art will appreciate that it can be used in the devices described herein.

In addition to the polymeric material, the balloon membrane 180 can include one or more optional coatings, for example one or more coatings to improve hydrophilicity of the membrane material, and/or reduce thrombogenicity and/or immunogenicity.

The tube 160 can also be formed of any suitable material. In non-limiting embodiments or aspects, the tube 160 is formed of a biocompatible, optionally in non-limiting embodiments or aspects biostable, polymer. In non-limiting embodiments or aspects, the tube 160 is formed of a polyimide or a polyimide-based material. As described in further detail below, the tube 160 can include a plurality of lumens. In non-limiting embodiments or aspects, one or more of the lumens is formed from a polyimide or a polyimide-based material, and the tube 160 can include, forming overlaying or otherwise covering at least a portion of the polyimide material (e.g., forming one or more additional lumens), a more flexible polymeric material. For example, and without limitation, tube 160 can include a guidewire lumen formed of a polyimide or a polyimide-based material, embedded or otherwise received within a more flexible polymer, such as a thermoplastic elastomer (as described herein or as known in the art), thermoplastic urethane, polyethylene terephthalate, silicone, and the like as known in the art for catheters, in particular cardiovascular catheters. Such materials can optionally include a radiopaque material, as is known in the art (and as also described herein).

Figure 2:
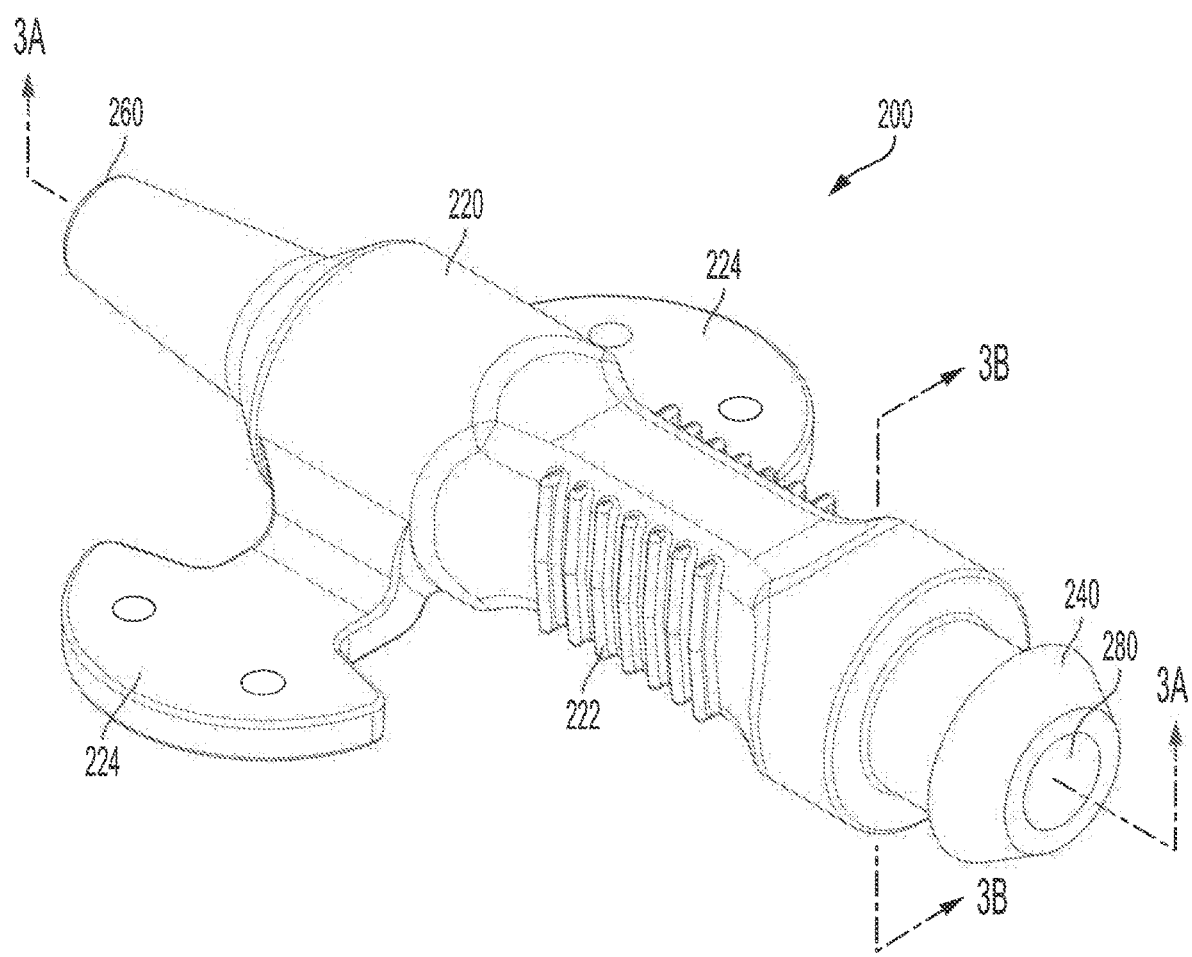
FIG. 2 is a perspective view of a sheath seal according to a non-limiting embodiment or aspect of the disclosure.
Figure 3A:
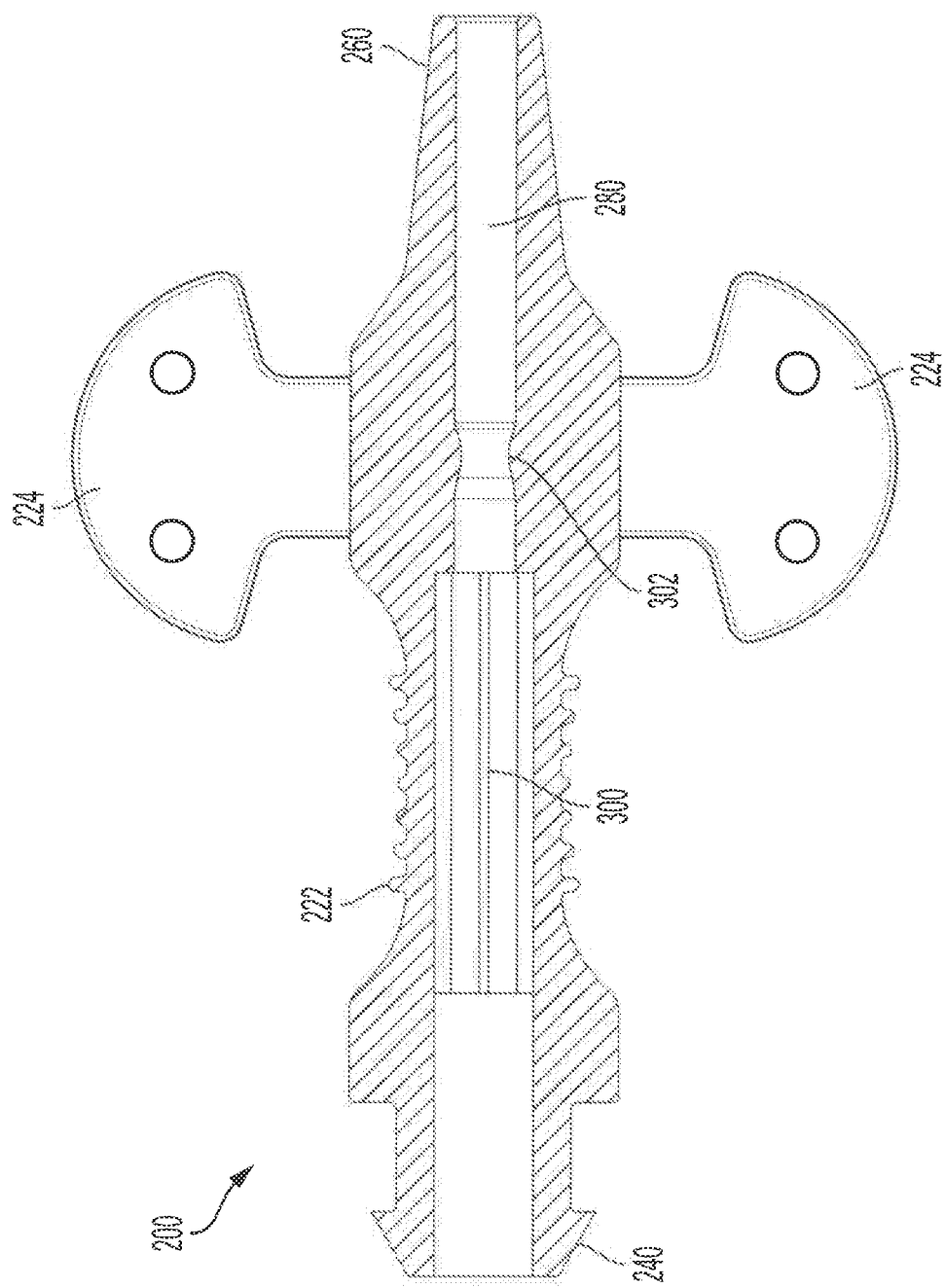
FIGS. 3A-3B are cross-sectional views of the sheath seal of FIG. 2 along lines 3A and 3B, respectively.
Figure 3B:
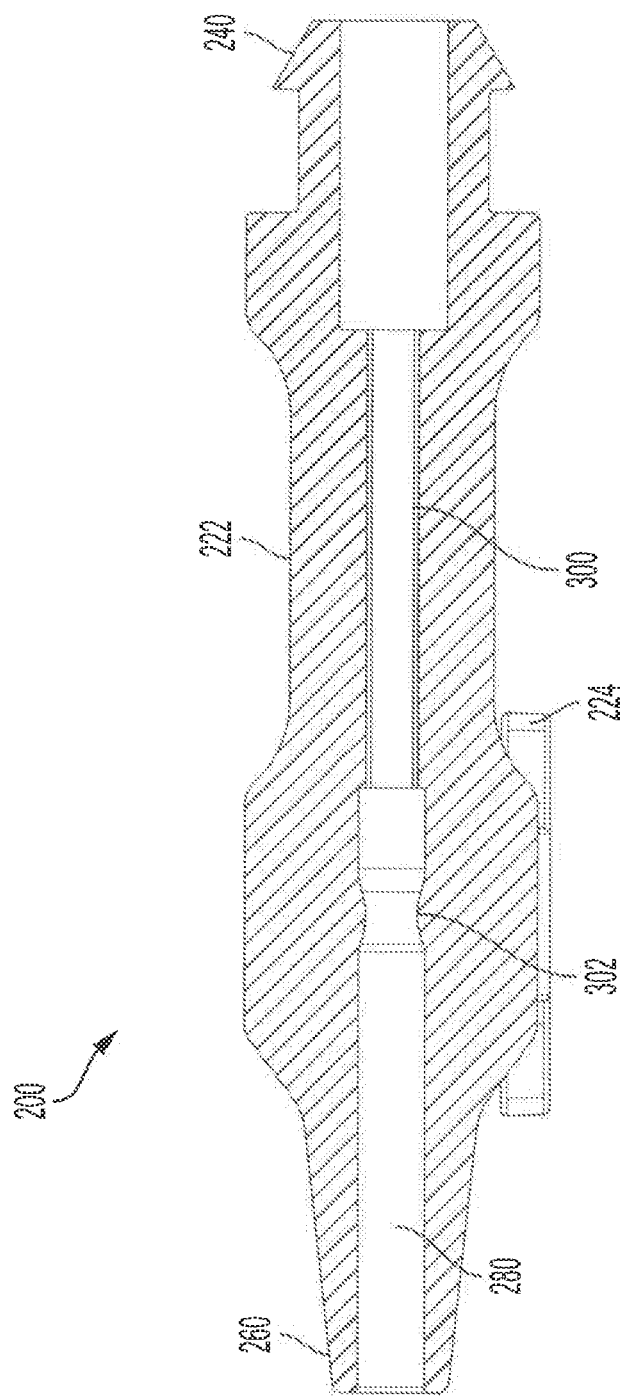

With continuing reference to FIG. 1, the balloon catheter assembly 1000 includes a sheath seal 200. With reference to FIGS. 2, 3A, and 3B, sheath seal 200 includes a housing 220 having a proximal end 240, a distal end 260, and a lumen 280 arranged between the proximal end 240 and the distal end 260. In non-limiting embodiments or aspects, distal end 260 of sheath seal housing 220 is tapered, its external surface narrowing in a distal direction. In non-limiting embodiments or aspects, the housing 220 is formed of an elastomeric material. In non-limiting embodiments or aspects, the housing 220 is formed of a thermoplastic elastomer. Those of skill in the art will appreciate that various elastomeric materials, including thermoplastic materials, will be suitable for the sheath seal 200. In non-limiting embodiments or aspects, the sheath seal housing 220 is formed of one or more of copolymers formed of a plastic and a rubber, including, for example and without limitation, styrenic block copolymers, thermoplastic polyolefin elastomers, thermoplastic vulcanizates, thermoplastic polyurethanes, thermoplastic polyesters, thermoplastic polyamides. Suitable thermoplastic elastomers are available commercially, for example, from PolyOne Corporation (e.g., the Versaflex™ series of thermoplastic elastomers, including G2705 N).

In non-limiting embodiments or aspects, sheath seal housing 220 includes one or more elements to allow attachment of the sheath seal 200 to a patient. In the non-limiting embodiment or aspect illustrated in FIGS. 2, 3A, and 3B, sheath seal housing 220 includes suture pads 224, to allow the sheath seal 200 to be attached to a patient's clothing or skin.

With continuing reference to FIGS. 2, 3A, and 3B, sheath seal 200 includes one or more impingement devices 300, 302. In non-limiting embodiments or aspects, sheath seal 200 includes two impingement devices 300, 302. Note that while FIGS. 3A and 3B show impingement devices 300, 302 in certain locations, devices as described herein may include one or both of impingement devices 300, 302. Use of more than one impingement device 300, 302 allows for a greater amount of total force applied to the outer surface 162 of catheter tube 160, while minimizing the total force at any one section of the tube 160, reducing occlusion of the lumen 166 (including, as discussed below, a gas lumen). Impingement device(s) 300, 302 impinge on (e.g., contact and engage, for example via friction and/or pressure) catheter tube 160, which is received within the lumen 280 of the housing 220. Impingement device(s) 300, 302 engage with catheter tube 160 with sufficient force, when employed alone or in combination, to resist movement or sliding of the catheter tube 160 during, for example, ambulatory heart-assist treatment.

Impingement device 300 is a variable impingement device and can assume a plurality of states that exert varying degrees of impingement force. In non-limiting embodiments or aspects, in a first state, impingement device 300 is engaged with catheter tube 160 and exerts a certain impingement force. In non-limiting embodiments or aspects, in a second state impingement device 300 is disengaged from, or otherwise not in contact with catheter tube 160, or at least not in substantial contact with catheter tube 160, thereby allowing catheter tube 160 to freely or readily slide within sheath seal lumen 280. In non-limiting embodiments or aspects, impingement device 300 may assume one or more additional states, for example, and without limitation, a third state where impingement device 300 remains engaged or in contact with catheter tube 160, but to a lesser degree (e.g., with a smaller impingement force) than the first state, such that catheter tube 160 may slide within sheath seal lumen 280, but such movement requires a greater pulling or pushing force to slide the catheter tube 160 than when the impingement device 300 is in the second state. In accordance with non-limiting embodiments or aspects of this disclosure, the first state, the third state, and the second state, may constitute a continuum characterized by how much force the impingement device(s) 300 exert upon the outer surface of the catheter tube 160.

Impingement device 302, on the other hand, is a static impingement device because the impingement force it exerts is essentially not variable. In other words, impingement device 302 has only one state so the impingement force it exerts is essentially static. In the non-limiting example of FIG. 3A, impingement device 302 constitutes a narrowing of lumen 280.

With continuing reference to FIGS. 2, 3A, and 3B, in non-limiting embodiments or aspects, sheath seal 200 includes one or more features that allow a user to change the state of the one or more impingement device(s) 300. In non-limiting embodiments or aspects, sheath seal housing 220 includes a collapsible section 222 arranged between the proximal 240 and distal 260 ends thereof, to which external pressure can be applied. In the illustrated embodiment of FIGS. 2, 3A, and 3B, pressure applied to collapsible portion 222 perpendicular to a longitudinal axis of the sheath seal housing 220 moves variable impingement device(s) 300 from a first state (as described above) to a second and/or third state (also as described above). In non-limiting embodiments or aspects, sheath seal housing 220 includes one or more tabs extending therefrom, such that application of pressure to the one or more tabs moves the impingement device to the second and/or third state from the first state.

Figure 8A:
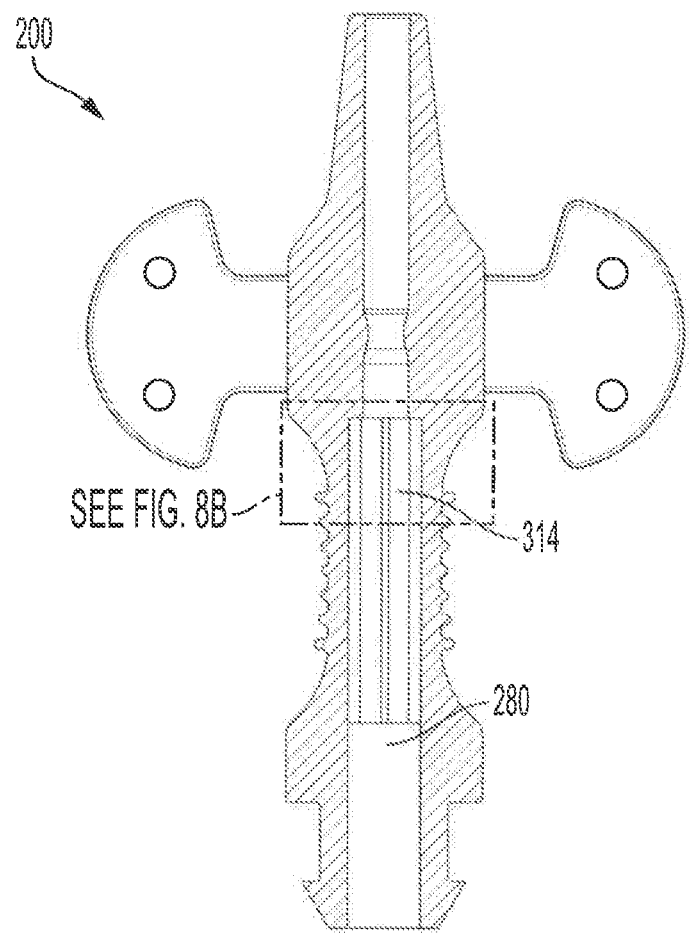
FIGS. 8A-8B are a top cross-sectional view (8A) and an enlarged view (8B) thereof of a non-limiting embodiment or aspect of an impingement device for use in a sheath seal of a balloon catheter assembly as described herein.
Figure 8B:
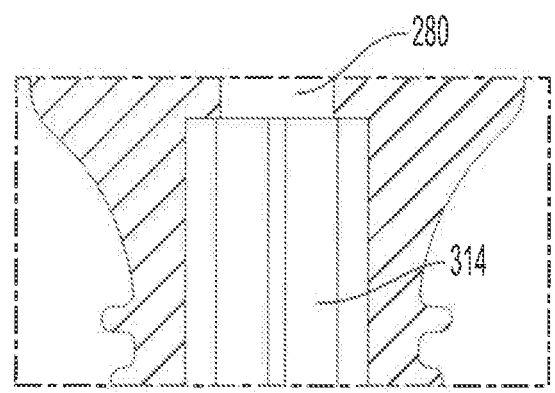

In non-limiting embodiments or aspects, with reference to FIGS. 8A, 8B, and 9-11, variable impingement device(s) 300 may include one or more moveable pressure elements that are configured to exert pressure on the outer surface 162 of the catheter tube 160. In non-limiting embodiments or aspects, the moveable pressure elements are one or more of an interference pinch lock 314 (FIGS. 8A and 8B), a bend 310 in the lumen 280 (FIG. 9), an off-axis center section and a channel 320 (FIG. 10) and/or an offset pinch (via tabs 330; FIG. 11). An interference pinch lock, for example as shown in FIGS. 8A and 8B, combines an internal interference fit (e.g., a friction fit or interference fit) that provides varying resistance when pinched and unpinched. Use of various materials can allow for designs providing higher interference forces, or a bigger change in interference force when pinched.

Figure 9:
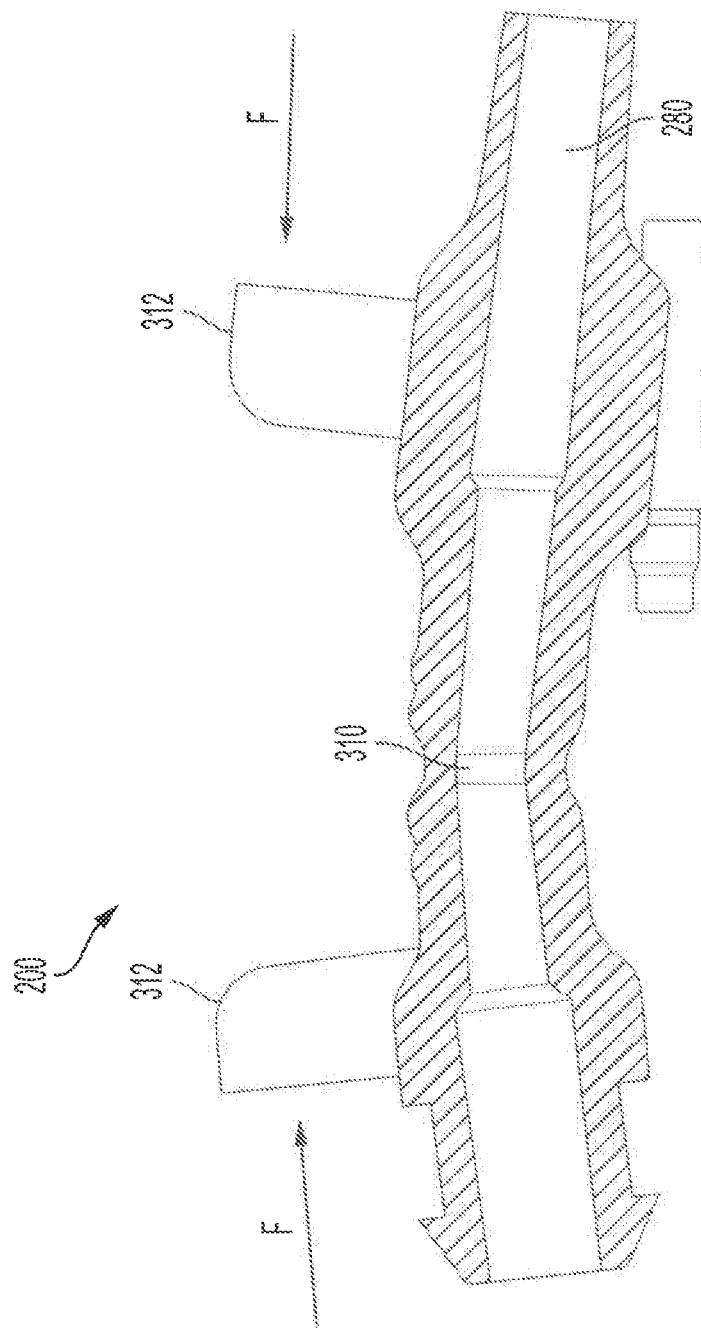
FIG. 9 shows a side cross-sectional view of a non-limiting embodiment or aspect of an impingement device for use in a sheath seal of a balloon catheter assembly as described herein.

A bend 310 in the lumen 280, for example as shown in FIG. 9, utilizes sections of the sheath seal housing 220 with local thinness, ensuring that deflections in the lumen 280 occur in locations providing interference between the catheter tube 160 and the sheath seal 200. By pinching tabs 312 to bring the tabs 312 closer together (e.g., pinching along the longitudinal axis of the housing 220 as evident from the arrows (F) in FIG. 9), the lumen 280 is straightened, allowing the catheter tube 160 to move freely within the sheath seal lumen 280. In this embodiment or aspect of the sheath seal 200, it is the bend 310 that promotes increased friction between the housing 220 and the outer surface 162 of the catheter tube 160, which serves to brake movement of the catheter tube 160 in the housing lumen 280 as a result of impingement.

Figure 10:
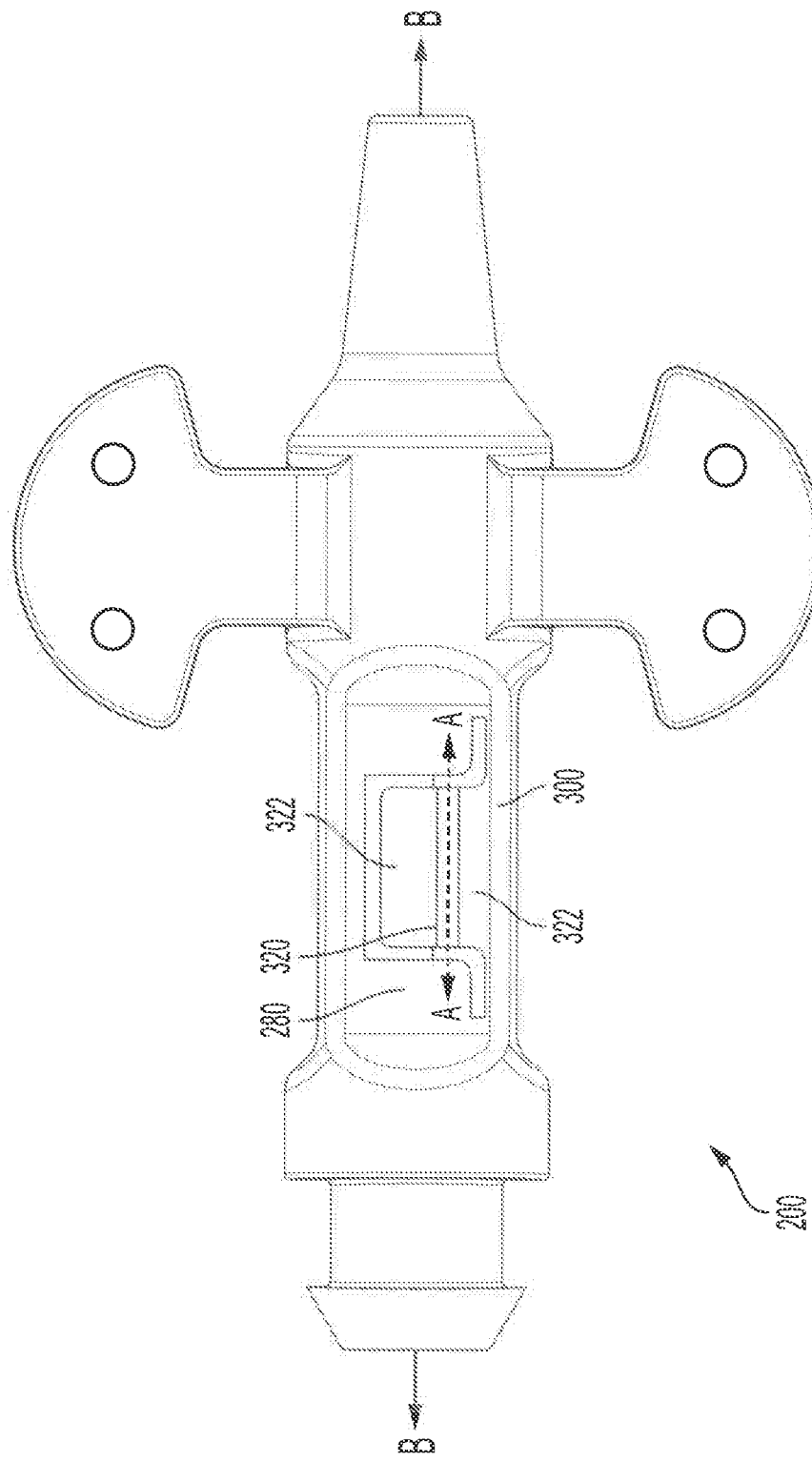
FIG. 10 shows a top, partial cross-sectional view of a non-limiting embodiment or aspect of an impingement device for use in a sheath seal of a balloon catheter assembly as described herein.

With reference to FIG. 10, in non-limiting embodiments or aspects, variable impingement device(s) 300 include a channel 320 defined by one or more sidewalls 322 that are disposed in the lumen 280 of the sheath seal 200. Note that FIG. 10 illustrates the sheath seal 200 without the catheter tube 160 in place. However, those of skill in the art will appreciate that the catheter tube 160 may be inserted through channel 320. In non-limiting embodiments or aspects, the channel 320 has a longitudinal axis A that is offset from a longitudinal axis B defined by the center of the sheath seal lumen 280. By pinching the center section of the sheath seal housing 220, longitudinal axes A and B become aligned thereby permitting insertion of the catheter tube 160 through channel 320. When the pinching force is removed from the center section of the sheath seal housing 220, then channel 320 moves towards its offset position so that longitudinal axes A and B are no longer aligned and, as a result, the impingement device(s) 300 exerts an impingement force against the outer surface of the catheter tube 160. Subsequently re-pinching the center section of the sheath seal housing 220 causes longitudinal axes A and B to re-align thereby removing the impingement force from the outer surface of the catheter tube 160, thereby freeing the catheter tube 160 and allowing movement thereof.

As evident from FIG. 10, when the center section of the sheath seal housing 220 is pinched so that longitudinal axes A and B are aligned, there is no impingement of the catheter tube 160 by the sidewalls 322 of the channel 320; however, when no pinch is applied to the center section of the sheath seal housing 220, then the longitudinal axis B of the channel 320 seeks to move out of alignment with longitudinal axis A of the lumen 280 and catheter tube 160 is impinged by the sidewalls 322 of the channel 320.

Figure 11A:
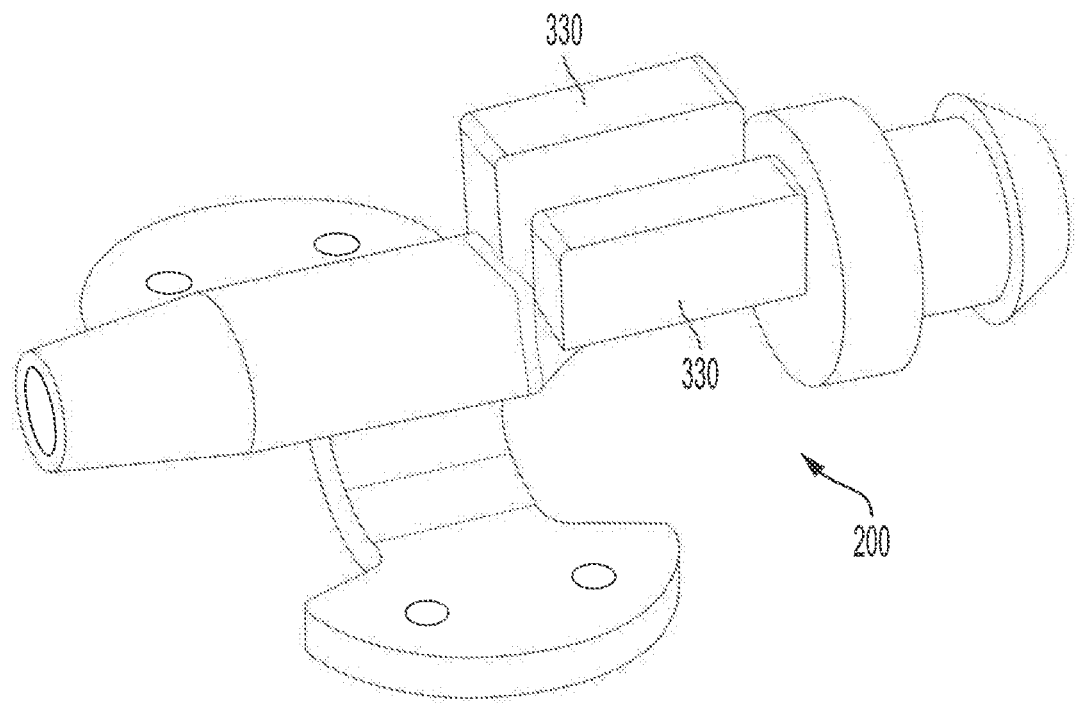
FIGS. 11A-11B show perspective (11A) and rear cross-sectional (11B) views of a non-limiting embodiment or aspect of an impingement device for use in a sheath seal of a balloon catheter assembly as described herein.
Figure 11B:
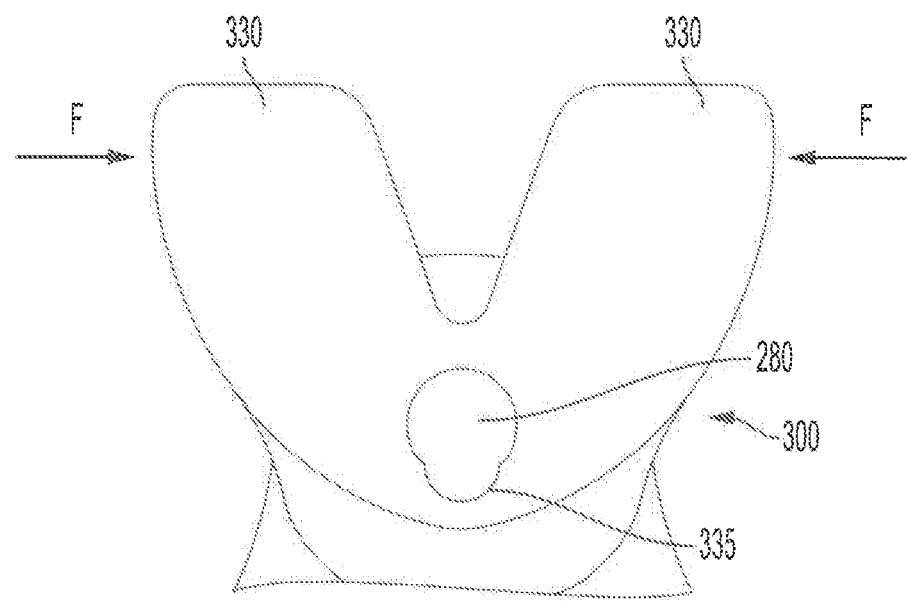

With reference to FIGS. 11A and 11B, a variable impingement device 300 employing an offset pinch (via tabs 330) arrangement is shown. Sheath seal lumen 280 is configured to maintain impinging interference around at least 270° of the catheter tube 160 because the diameter of lumen 280, or at least a portion of lumen 280, is slightly smaller than the diameter of the catheter tube 160 so that the inner surface of the lumen 280 exerts an impingement force on the outer surface of the catheter tube 160. By squeezing tabs 330 together (e.g., perpendicular to a longitudinal axis of the sheath seal 200 as evident by the arrows (F) pointing towards each other), impinging interference is relieved, at least in part, by virtue of notch 335 contiguous with lumen 280, thus allowing for an increase in the diameter of the lumen 280 when tabs 330 are pinched towards each other, and catheter tube 160 is freed for movement.

With reference to FIGS. 1 and 3A, assembly 1000 includes, in non-limiting embodiments or aspects, one or more valves 302 within sheath seal 200. Such valves, which may constitute fixed impingement devices, allow for multiple devices to be used and secured during treatment, such as heart-assist treatment.

Figure 4B:
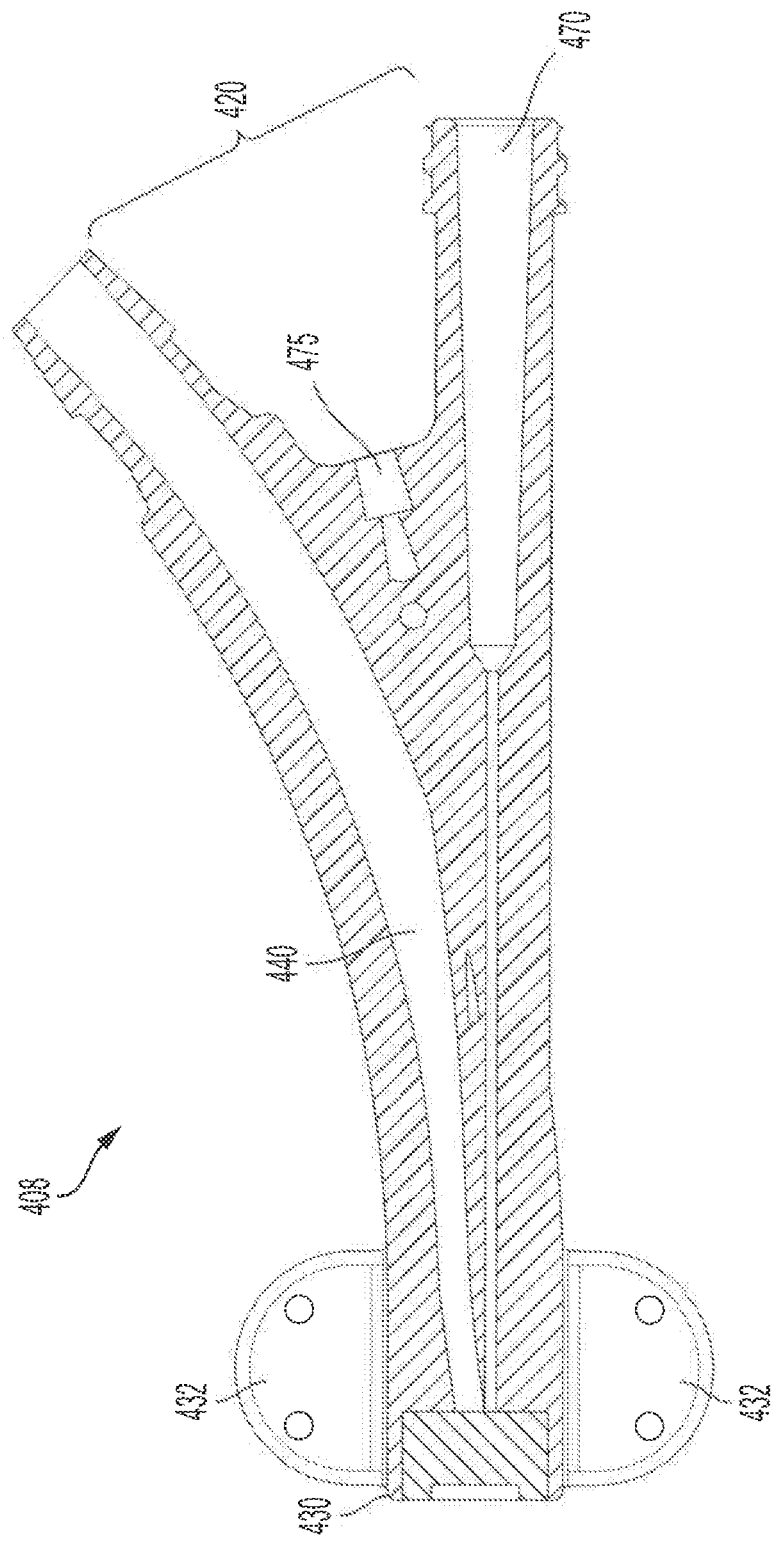
FIG. 4B is a cross-sectional view of the y-connection of FIG. 4A along line 4B.

With reference to FIGS. 4A and 4B, y-connection assembly 400 includes a hub 406 and y-connection 408 having a proximal end 420, a distal end 430, and a lumen 440 arranged therebetween. Lumen 440 is configured to carry gas for operating balloon membrane 180, and includes a narrowing or tapering disposed therein. In non-limiting embodiments or aspects, y-connection 408 includes one or more elements to allow attachment to a patient. In the non-limiting embodiment or aspect illustrated in FIGS. 4A and 4B, y-connection 408 includes suture pads 432, to allow the y-connection 408 to be attached to a patient's clothing or skin. In non-limiting embodiments or aspects, hub 406 is connected, removably or fixedly, to sheath seal housing 220.

In non-limiting embodiments or aspects, y-connection 408 includes an angularly extending or curved main section 412 and an elongated section 414. Proximal end(s) of the main section 412 and/or elongated section 414 can include connections as are known in the art, for example, and without limitation, luer connections (male or female). In non-limiting embodiments or aspects, between the proximal end 420 of the y-connection 408 and the distal end 260 of the sheath seal 200 there extends a gas lumen 440 that is angled with respect to one or both of the sheath seal lumen 280 and the y-connection 408, and which is formed by contiguous arrangement of the sheath seal lumen 280 so lumen 440 and sheath seal lumen 280 are contiguous with each other. In non-limiting embodiments or aspects, lumen 440 is arranged in main section 412, and thus is angled with respect to the lumen 280 of the sheath seal 200. A guidewire lumen 470 is disposed within the elongated section 414 and is configured to permit passage of a guidewire therethrough. Thus, the guidewire lumen 470 is configured to connect either directly or indirectly with the guidewire lumen 172 of the catheter tube 160 so that a guide wire may be passed through guidewire lumen 470 and into guidewire lumen 172 and then into lumen 143 of curved portion 142.

In non-limiting embodiments or aspects, y-connection 408 includes sensor cable lumen 475 through which a sensor cable (not shown) extends and connects with sensor 190 via sensor lumen 168 of catheter tube 160. FIG. 4B shows only portions of the sensor cable lumen 475 that winds its way through y-connection 408 to the sensor lumen 168 of catheter tube 160.

Figure 5A:
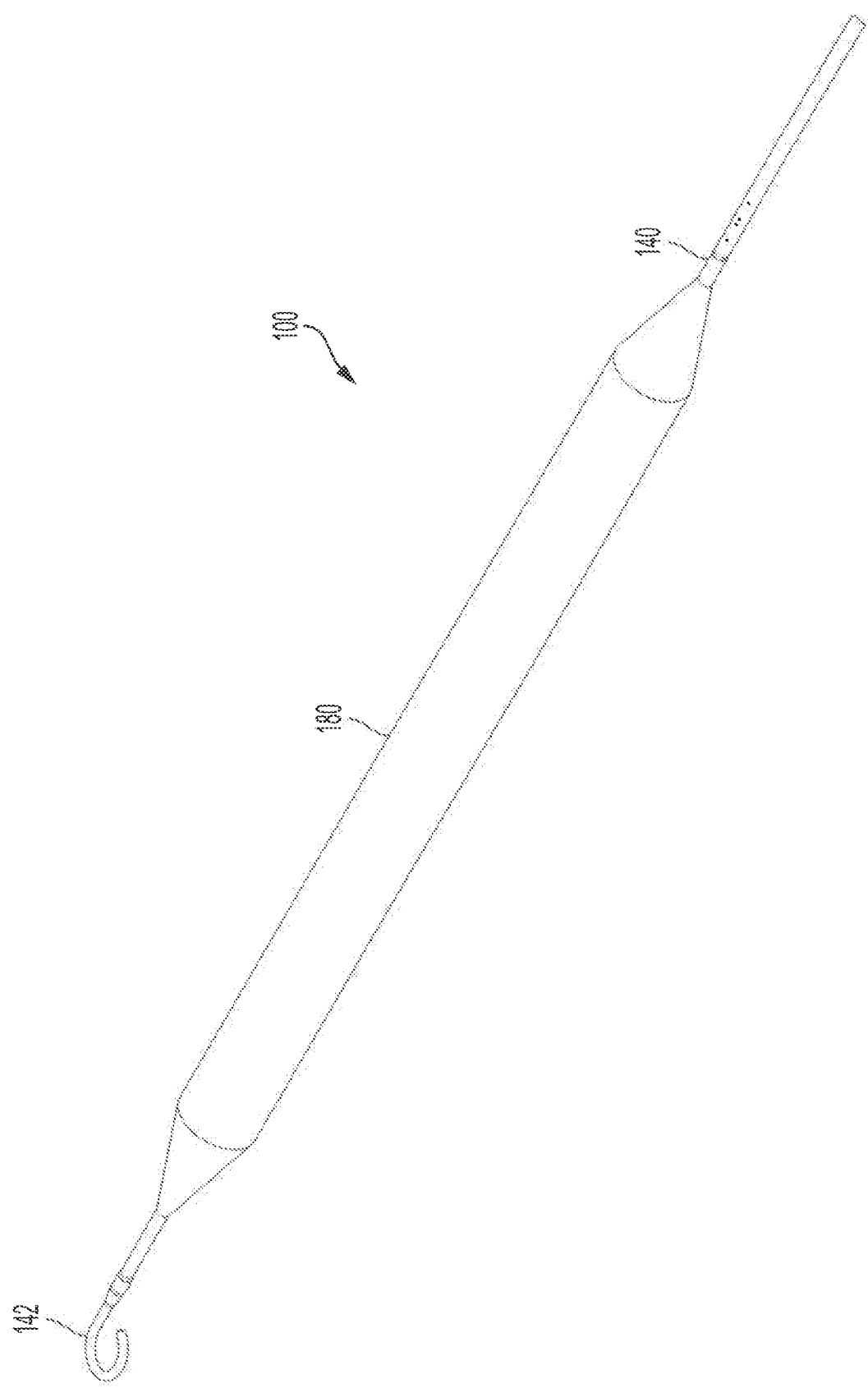

With continuing reference to FIG. 1, as described above, assembly 1000 includes IABP 100. With reference to FIGS. 5A and 5B, in non-limiting embodiments or aspects, IABP 100 includes, at a distal end of membrane 180, a curved portion 142 that may be configured as a J-tip or a pigtail.

When used in methods described herein (e.g., for introduction into a patient for heart-assist therapy), curved portion 142 of IABP 100 can prevent the distal end of the balloon membrane 180 from undesirably entering a blood vessel, such as the superior mesenteric artery (SMA), during ambulatory heart-assist treatment or other event(s) that may cause migration of the IABP 100. In non-limiting embodiments or aspects, curved portion 142 is a pre-formed curve, such that the curved portion 142 substantially or completely exhibits its final shape prior to insertion of the IABP 100 into a patient. In non-limiting embodiments or aspects, the curved portion is a pre-formed j-tip. A j-tip is so named due to its appearance.

In non-limiting embodiments or aspects, and with reference to FIG. 5B, the curved portion 142, or j-tip, includes a first substantially straight section 144, a curved section 146 connected at a first end thereof to a distal end of the first straight section 144, and a second substantially straight section 148 connected at a proximal end thereof to a distal end of the curved section 146. In non-limiting embodiments or aspects, second substantially straight section 148 is substantially or completely parallel to first substantially straight section 144. In non-limiting embodiments or aspects, one or more additional curved and/or straight sections may extend from a distal end of the second substantially straight section 148. In non-limiting embodiments or aspects, curved portion 142 forms a theoretical circle, completed with hatched lines shown in FIG. 5B, which may be characterized as a pigtail. In non-limiting embodiments or aspects, a diameter of such a theoretical circle is greater than 8 mm, for example, 9 mm, 10 mm, or 11 mm. A typical branch off of an aorta has a diameter of 5-7 mm (renal arteries) or 6-8 mm (SMA and celiac trunk), thus, a diameter of greater than such a radius aids in preventing the balloon membrane 180 and IABP 100 from undesirably entering a branch of the aorta during placement and/or treatment.

In non-limiting embodiments or aspects, curved portion 142 is formed of a thermoplastic, such as a thermoplastic elastomer as described above. In non-limiting embodiments or aspects, curved portion 142 is formed of or at least partially includes a thermoplastic polyurethane. In non-limiting embodiments or aspects, curved portion 142 is formed of a polyether-based thermoplastic polyurethane. Such materials are commercially available from, for example, Lubrizol Corporation (e.g., the Estane® series of thermoplastic polyurethanes, including Estane® 58887). In non-limiting embodiments or aspects, the curved portion 142 is formed of or at least partially includes a metal, such as a shape-memory alloy. In non-limiting embodiments or aspects, the curved portion 142 comprises one or more radiopaque materials, such as, for example and without limitation, barium, e.g., barium sulfate. Other suitable radiopaque materials are known to those of skill in the art.

In non-limiting embodiments or aspects, the j-tip is configured so as to include a portion that is not curved and that is radiopaque because it is made of a blend of Pelethane® 5855 (an aromatic polyester-based thermoplastic polyurethane) and tungsten particles. In non-limiting embodiments or aspects, the j-tip configuration may include a flexible "white" portion that is curved and made of Estane® 58887 blended with $BaSO_4$ and a "black" straight portion (to which a membrane is bonded via plastic welding) made from Pelethane® 5855 blended with tungsten particles, both of which are molded onto the end of the polyimide inner lumen of the j-tip.

In non-limiting embodiments or aspects (not shown), rather than curved portion 142, a distal end of IABP 100 can include an elongated section. The elongated section may have a length of 120 mm to 210 mm, optionally 130 mm to 200 mm, and all subranges therebetween inclusive. Without wishing to be bound by one particular theory, it is believed that such an elongated extension would reside in a common iliac artery, thus preventing the IABP 100 from entering a side branch of the aorta during placement and/or treatment.

With further reference to FIG. 5B, curved portion 142 can include a lumen 143 therein, to allow a guidewire, for example a guidewire used during placement of IABP 100, to enter therein because lumen 143 of the curved portion 142 is contiguous with lumen 166 of catheter tube 160, or in particular guidewire lumen 172 of lumen 166, which is contiguous with sheath seal lumen 280 and lumen 470 of the y-connection 408. Entry of a guidewire into lumen 143 can temporarily straighten curved portion 142, which can return to its pre-formed curve once the guidewire is withdrawn from lumen 143.

Figure 6B:
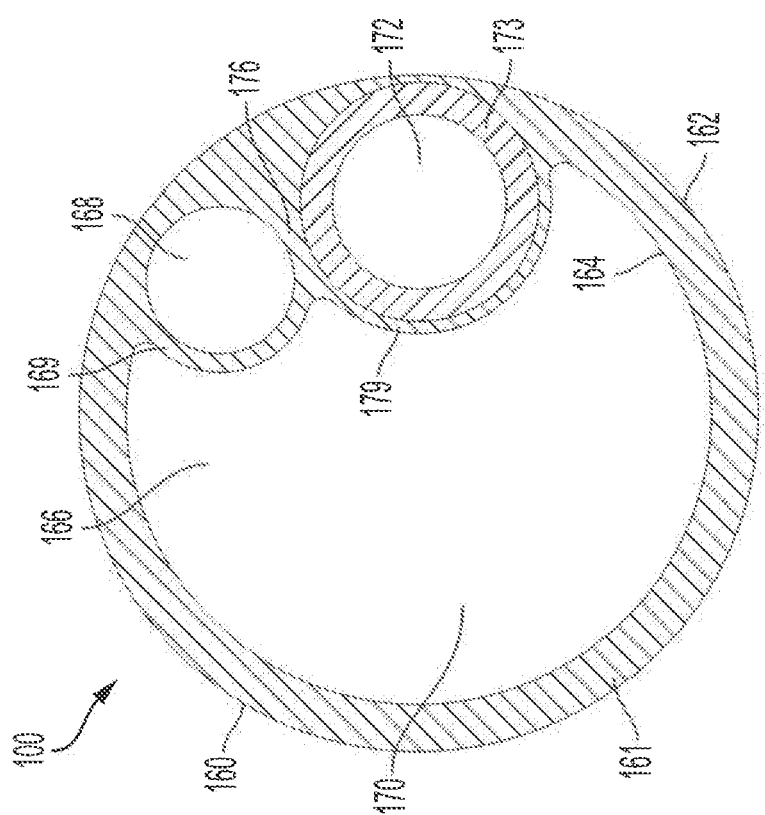
FIG. 6B is a cross-sectional view of the balloon catheter of FIG. 6A along line 6B.

As described briefly above, catheter tube 160 can include a plurality of lumens therethrough. With reference to FIGS. 6A and 6B, shown is IABP 100 (FIG. 6A) and a cross-section therethrough (FIG. 6B). In the non-limiting embodiment or aspect shown in FIG. 6B, catheter tube 160 includes a lumen 166 that is partitioned into a sensor lumen 168, a gas lumen 170, and a guidewire lumen 172. In non-limiting embodiments or aspects, for example in aspects where the IABP 100 is not delivered over a guidewire, lumen 172 can be employed as a second sensor lumen. In non-limiting embodiments or aspects, one or more of the sensor lumen 168, gas lumen 170, and guidewire lumen 172 have a cross-sectional diameter that varies along the length of IABP 100.

In non-limiting embodiments or aspects, guidewire lumen 172 is in communication with lumen 143 of curved portion 142, such that a guidewire passing through guidewire lumen 172 can enter lumen 143 of curved portion 142. As also discussed above, guidewire lumen 172 can be formed of a different material than catheter tube 160, for example, and without limitation, a polyimide, so as to form its own distinct tube. Thus, guidewire lumen 172 can include a sidewall 173 formed of a polyimide and embedded in another material making up the circular wall of catheter tube 160, in which is formed sensor lumen 168 and/or gas lumen 170. In non-limiting embodiments or aspects, the guidewire lumen 172 and gas lumen 170 are arranged in a co-lumen (e.g., one lumen arranged within another lumen) arrangement because they are formed within the outer wall 161 of catheter tube 160 as internal partitions of lumen 166. In non-limiting embodiments or aspects, guidewire lumen 172 and sensor lumen 168 share a common sidewall 176. In non-limiting embodiments or aspects, sensor lumen 168 includes sensor lumen sidewall 169. In non-limiting embodiments or aspects, sensor lumen 168 and gas lumen 170 are arranged in a co-lumen (e.g., one lumen arranged within another lumen) arrangement because they are formed within the outer wall 161 of catheter tube 160 as internal partitions of lumen 166. In non-limiting embodiments or aspects, sensor lumen 168 includes one or more apertures 174 in a sidewall 161 thereof. In non-limiting embodiments or aspects, sensor lumen 168 includes four apertures 174a, 174b, 174c, 174d in its sidewall 161 so that a sensor 190 in sensor lumen 168 is able to measure pressure in vasculature in which catheter tube 160 has been placed in view of one or more of the apertures 174 that open to space external to the catheter tube 160.

With continuing reference to FIGS. 6A and 6B, gas lumen 170 is in fluid communication with the interior of balloon membrane 180, allowing for the passage of an inflating gas thereto and therefrom, thus allowing for cyclical inflation and deflation of the balloon membrane 180 of the IABP 100 to deliver heart-assist treatment. By arranging and configuring the gas lumen 170 as described herein, increased speed and efficiency in filling and emptying the balloon membrane 180 can be achieved, increasing therapeutic efficiency of the IABP 100. In non-limiting embodiments or aspects, a maximum diameter of the gas lumen 170 is greater than the maximum diameter of the guidewire lumen 172, which is greater than the maximum diameter of the sensor lumen 168. In non-limiting embodiments or aspects, a cross-sectional surface area of the gas lumen 170 is greater than a cross-sectional surface area of the guidewire lumen 172, which is greater than a cross-sectional surface area of the sensor lumen 168. In non-limiting embodiments or aspects, the sensor lumen 168 has a circular cross sectional area, the guidewire lumen 172 has a circular cross sectional area that is larger than the circular cross sectional area of the sensor lumen 168, and the gas lumen 170 has a non-circular cross section that is at least twice the area of the combined cross sectional areas of the sensor lumen 168 and the guidewire lumen 172.

Figure 7A:
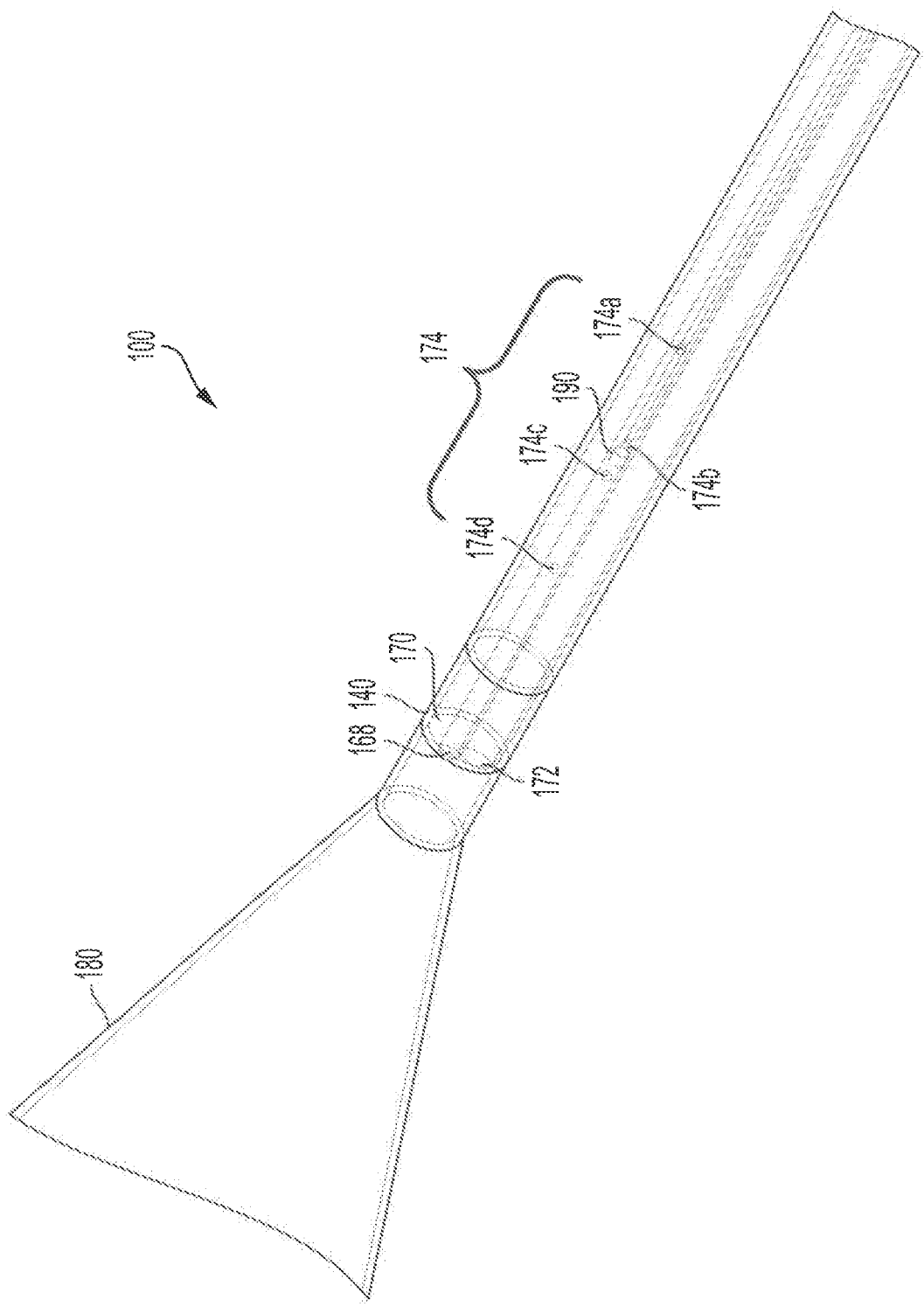
FIG. 7A is a perspective, partial transparent view of a balloon catheter according to a non-limiting embodiment or aspect of the disclosure.
Figure 7B:
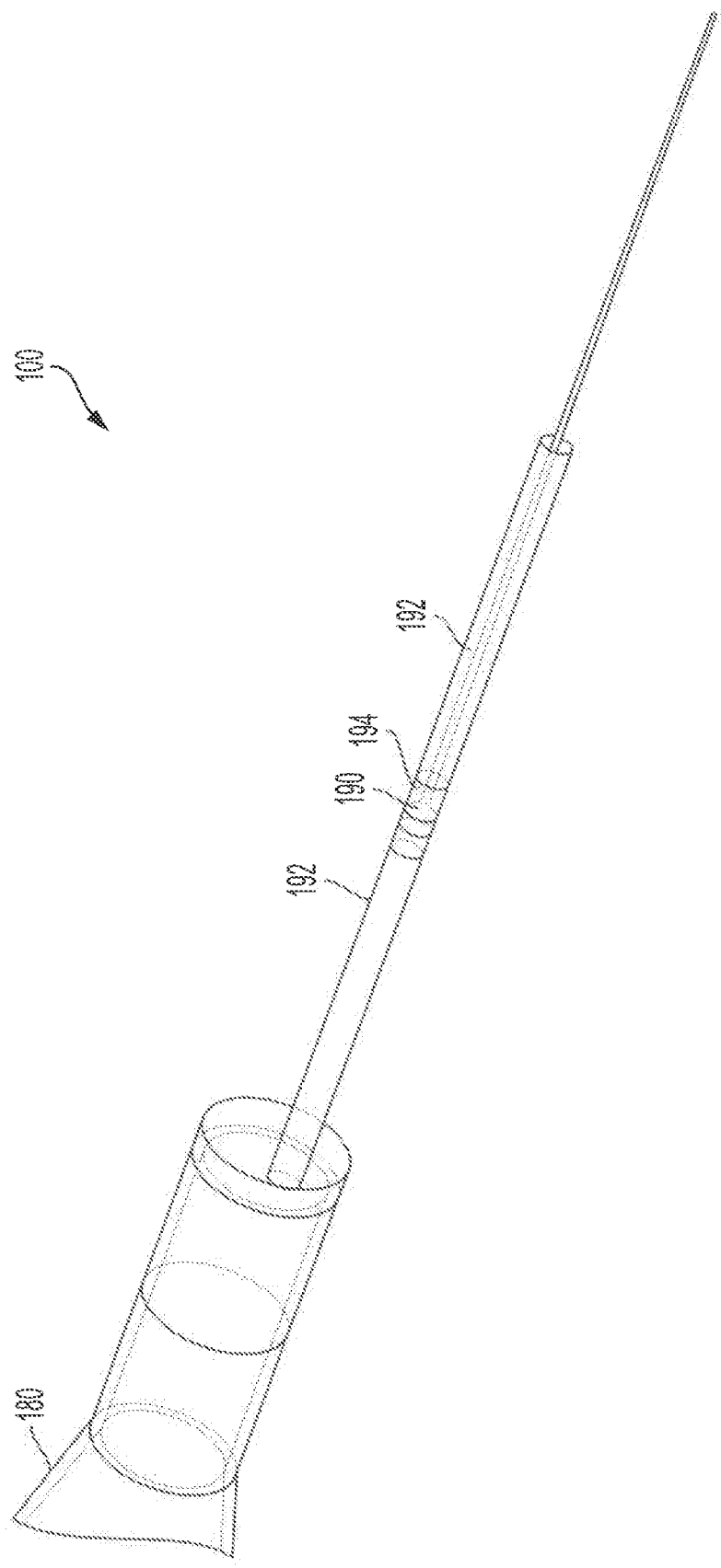
FIG. 7B is a perspective view of the balloon catheter of FIG. 7A with a portion of the catheter sidewall hidden to allow for a clearer view of a sensor assembly according to a non-limiting embodiment or aspect of the disclosure.

Turning to FIGS. 7A and 7B, in non-limiting embodiments or aspects, assembly 1000, including IABP 100, includes a sensor 190. Sensor 190 can be a pressure sensor, for example and without limitation, for sensing blood pressure in the vessel(s) in which the IABP 100 is disposed. In non-limiting embodiments or aspects, sensor 190 is a fiber-optic pressure sensor, such as that used with the CS300™ IABP from Maquet/Getinge. Sensor 190 can be disposed in sensor lumen 168 in embodiments or aspects including in those employing a catheter tube 160 having a plurality of lumens. In non-limiting embodiments or aspects, sensor 190 is disposed in catheter tube 160, for example in sensor lumen 168, at a distal end 140 of catheter tube 160, proximal of the balloon membrane 180, in some non-limiting embodiments or aspects near the base (proximal-most end) of balloon membrane 180. Without intending to be bound by a particular theory, it is believed that positioning the sensor 190 in this manner, when combined with the shorter length of an IABP 100 as described herein, allows for the sensor 190 to be positioned in a similar manner (relative to the patient's aortic valve) to current IABPs, which are of a significantly greater length.

In non-limiting embodiments or aspects, sensor 190 can sense blood pressure based at least in part on the presence of aperture(s) 174 located in the wall of catheter tube 160, in particular in certain embodiments or aspects in the sidewall 161 of sensor lumen 168. In non-limiting embodiments or aspects, sensor 190 is disposed in sensor lumen 168 and is located in a pocket between two segments of a cured adhesive 192. Adhesive 192 can be any biocompatible adhesive, whether biostable or not, so long as it is capable of holding sensor 190 in a suitable location within sensor lumen 168. In non-limiting embodiments or aspects, adhesive 192 is one or more of an acrylic adhesive, an epoxy adhesive, a silicone adhesive, and/or a styrene block co-polymer adhesive. As described above, sensor lumen 168 can include a plurality of apertures 174, for example, and without limitation, four apertures 174, as shown in FIG. 7A. Sensor 190 can be arranged in sensor lumen 168, such that adhesive 192 can be introduced into the proximal-most aperture 174a and distal-most aperture 174d, to hold sensor 190 in place. Innermost apertures 174b and 174c can then be used by sensor 190 to detect pressure in a vessel in which IABP 100 is positioned because these apertures permit fluidic communication of pressure between the pocket in which the sensor 190 sits in sensor lumen 168 and blood flowing outside of the outer surface 162 of the catheter tube 160 when the catheter tube is disposed in vasculature of a patient. Pressure measured in the gas lumen 170 using other pressure sensors may be used to ascertain arterial pressure in the artery in which the balloon membrane 180 is positioned in order to calibrate the sensor 190 in accordance with a known technique described by U.S. Patent 7,771,362, which is incorporated herein by reference in its entirety. In accordance with an aspect of this disclosure, innermost apertures 174b and 174c may also be used to introduce a gel 194 into the sensor lumen 168.

With continuing reference to FIG. 7B, in non-limiting embodiments or aspects, sensor 190 is surrounded by a gel 194, for example, and without limitation, a viscous gel, for example and without limitation, a silicone gel. In non-limiting embodiments or aspects, gel 194 is introduced into the pocket between adhesives 192 in which sensor 190 is positioned. Gel 194 can be introduced into the pocket, with reference to FIG. 7A, through innermost apertures 174b and/or 174c. The gel 194 is one suitable for transmitting pressure from space external to the catheter tube 160 to the sensor 190 in the pocket of sensor lumen 168.

In view of the foregoing, also provided herein is an intra-aortic balloon catheter, for example a catheter 100 as shown in FIGS. 1, 5A, 6A, and 6B, including a proximal end 120, a distal end having a curved portion 142, or j-tip, a tube 160 arranged between the proximal end 120 and the distal end and having an outer surface 162 and an inner surface 164 defining one or more lumens 166, and a balloon membrane 180 disposed at the distal end, proximal of the curved portion 142, or j-tip. As described above, catheter 100 can have any suitable length, but is, in certain non-limiting embodiments or aspects, less than 18 inches in length, and, in certain non-limiting embodiments or aspects, 14-18 inches in length. As described above, and as shown in the non-limiting embodiment or aspect of FIG. 6B, catheter tube 160 can include a sensor lumen 168, a gas lumen 170, and a guidewire lumen 172. In non-limiting embodiments or aspects, as described above, guidewire lumen can be formed of a more rigid polyimide material, embedded or otherwise received within a more flexible polymer that makes up the remainder of catheter tube 160. The guidewire lumen 172 (e.g., a polyimide tube) can be in a co-lumen arrangement with gas lumen 170. Sensor lumen 168 can include one or more apertures 174, as described previously and as shown in FIG. 7A. Sensor lumen 168 may also be in a co-lumen arrangement with gas lumen 170. Guidewire lumen 172 and sensor lumen 168 can share a common sidewall 176. Thus, the gas lumen 170 may be defined by a portion of the inner surface 164 of the catheter tube 160 and by the sensor lumen sidewall 169 and the sidewall 179 enveloping guidewire tube 173. The inner surface 164, the sensor lumen sidewall 169 and the sidewall 179 are made of the same material. The guidewire lumen 172 is formed by the tube 173, which is preferably made of a different material than that of the sidewall 161 forming the inner and outer surfaces 164, 162 of the catheter tube 160. The sensor lumen 168 is defined by the sensor lumen sidewall 169, the common sidewall 176, and a portion of sidewall 161, which are all made of the same material.

As described previously, and with regard to FIG. 5B, the curved portion 142, or j-tip, includes a first substantially straight segment 144, a curved segment 146 connected at a first end thereof to a distal end of the first straight segment 144, and a second substantially straight segment 148 connected at a proximal end thereof to a distal end of the curved segment 146. In non-limiting embodiments or aspects, second substantially straight segment 148 is substantially or completely parallel to first substantially straight segment 144. In non-limiting embodiments or aspects, one or more additional curved and/or straight segments may extend from a distal end of the second substantially straight segment 148. In non-limiting embodiments or aspects, the j-tip forms a theoretical circle, completed with hatched lines shown in FIG. 5B. In non-limiting embodiments or aspects, a diameter of such a theoretical circle is greater than 8 mm, for example 9 mm, 10 mm, or 11 mm. As also described above, the curved portion 142, or j-tip, can include one or more radiopaque materials therein. In non-limiting embodiments or aspects, the curved portion 142, or j-tip, is formed of a thermoplastic, such as a thermoplastic elastomer as described above. In non-limiting embodiments or aspects, the curved portion 142, or j-tip, is formed of or at least partially includes a metal, such as a shape-memory alloy.

The intra-aortic balloon catheter can further include a sheath seal 200, as shown in FIGS. 1, 2, 3A, and 3B. With reference to FIGS. 2, 3A, and 3B, sheath seal 200 can include a housing 220 having a proximal end 240, a distal end 260, and a lumen 280 arranged between the proximal end 240 and the distal end 260. In non-limiting embodiments or aspects, distal end 260 of sheath seal housing 220 is tapered, narrowing externally in a distal direction. In non-limiting embodiments or aspects, the housing 220 is formed of an elastomeric material. In non-limiting embodiments or aspects described above, the housing 220 is formed of a thermoplastic elastomer. Sheath seal 200 can also include one or more variable impingement devices 300 and/or one or more static impingement devices 302. In non-limiting embodiments or aspects, sheath seal 200 includes two impingement devices 300, 302. As described above, impingement device(s) 300, 302 impinge on (e.g., contact and engage, for example via friction and/or pressure) catheter tube 160, which is received within the lumen 280. Impingement device(s) 300, 302 engage with catheter tube 160 with sufficient force to resist movement or sliding of the catheter tube 160 during, for example, ambulatory heart assist treatment. In accordance with this disclosure, when multiple impingement devices are employed, more than one of the same impingement device may be employed and/or different impingement devices may be employed at the same time in order to achieve sufficient force to resist movement or sliding of the catheter tube 160.

As described above, catheter 160 can include a sensor 190 disposed in sensor lumen 168, arranged/positioned in a gap or pocket between two segments of a cured adhesive 192. Sensor 190 can be surrounded by a gel 194, for example a viscous silicone gel. Sensor 190 can be positioned at a distal-most end of catheter tube 160, proximal (and in some non-limiting embodiments or aspects, immediately adjacent to proximal end of) balloon membrane 180.

Also provided herein, and referencing FIGS. 1 and 6B, is an intra-aortic balloon catheter 100 including a proximal end 120, a distal end 140, a tube 160 having a sidewall 161 having an outer surface 162 and an inner surface 164 defining a gas lumen 170, a sensor lumen 168 in a co-lumen arrangement with the gas lumen 170, and a guidewire lumen 172 in a co-lumen arrangement with the gas lumen 170 and sharing a common sidewall 176 with the sensor lumen 168. In non-limiting embodiments or aspects, proximal end 120 is bifurcated (e.g., two proximal ends) or trifurcated (e.g., three proximal ends). In non-limiting embodiments or aspects, the number of proximal ends matches the number of lumens within the tube 160 of the intra-aortic balloon catheter 100. For example, and without limitation, one proximal end that includes gas lumen 440 may be connected to a gas source so as to inflate and deflate the balloon membrane via gas lumen 170, while one of the ends has an opening for guidewire lumen 470 that is contiguous with guidewire lumen 172 so a guidewire may be inserted therein. There may be a third end, or at least a channel 475, that is associated with the sensor 190 and sensor lumen 168. The intra-aortic balloon catheter 100 includes a balloon membrane 180 disposed at the distal end 140 of the tube 160 and in fluid communication with the gas lumen 170. As described above, catheter 100 can have any suitable length, but is, in certain non-limiting embodiments or aspects, less than 18 inches in length, and in certain non-limiting embodiments or aspects 14-18 inches in length. As described above, distal end of catheter 100, distal of balloon membrane 180, can include a curved portion 142, or j-tip. As also described above, the curved portion 142, or j-tip, can include a lumen 143 to allow a guidewire, for example a guidewire that passes through guidewire lumen 172, to be received therein.

As noted previously, assemblies/devices/catheters described herein are useful for methods of providing heart-assist treatment, for example right-heart assist treatment and/or left-heart assist treatment. Catheters and assemblies as described herein may be used with known systems (e.g., computer-controlled heart-assist treatment systems), such as, for example and without limitation, CS300™ and CARDIOSAVE from Maquet/Getinge, to provide heart-assist treatment. In non-limiting embodiments or aspects, based on one or more of the curved portion/j-tip, cured adhesive in the sensor lumen, suture pads of the sheath seal and/or y-connection, and the shorter catheter length, which allows access to the vasculature that is closer in proximity to the heart through the axillary or subclavian arteries, assemblies/devices/catheters provided herein are useful for ambulatory heart-assist treatment. By ambulatory it is meant that, unlike prior heart-assist treatment protocols, where a patient is limited to a supine position, a patient receiving heart-assist treatment can be seated in an upright positon, standing, and/or moving (i.e., ambulating).

A method of providing heart assist by intravascular balloon pumping of blood includes the steps of inserting into a patient's vasculature, an intra-aortic balloon catheter or IABP as described above. In non-limiting embodiments or aspects the IABP is inserted into the patient's axillary artery or subclavian artery. The IABP includes a proximal end, a distal end, a tube arranged between the proximal end and the distal end and having an outer surface and an inner surface defining one or more lumens, and a balloon membrane disposed at the distal end and in fluid communication with at least one of the one or more lumens. The IABP may also include a sheath seal as described above, the sheath seal having an elastomeric housing having a proximal end, a distal end, and a lumen arranged between the proximal end and the distal end. The housing includes one or more impingement devices that engage the outer surface of the catheter tube that is received in the lumen of the sheath seal and the one or more impingement devices apply a force to the outer surface the catheter tube. The method further includes the step of advancing the distal end of the IABP to the patient's aorta (for left-heart assist), and cyclically inflating and deflating the balloon membrane by passing a fluid (such as helium gas) through at least one of the one or more lumens. In non-limiting embodiments or aspects, as described above, the sheath seal can include one or more suture pads to allow the sheath seal to be secured to the patient. In non-limiting embodiments or aspects of the method, a further step includes securing the sheath seal to the patient.

Although the devices, assemblies, and methods have been described in detail for the purpose of illustration based on what is currently considered to be the most practical and preferred embodiments, it is to be understood that such detail is solely for that purpose and should not be considered limiting, but on the contrary, is intended to cover modifications and equivalent arrangements that are within the spirit and scope of the appended claims. For example, it is to be understood that the present systems and methods contemplate that, to the extent possible, one or more features of any embodiment can be combined with one or more features of any other embodiment.

The invention claimed is:

1. A balloon catheter assembly comprising:
   an intra-aortic balloon catheter comprising a proximal end, a distal end, and a tube arranged between the proximal end and the distal end, wherein the tube has an outer surface and an inner surface defining at least one lumen extending between the proximal end and the distal end, and a balloon membrane is disposed at the distal end; and
   a sheath seal comprising an elastomeric housing comprising a proximal end, a distal end, a lumen of the sheath seal arranged between the proximal end of the housing and the distal end of the housing, wherein the housing comprises an impingement device, wherein the lumen of the sheath seal is configured to slidably receive the tube therein and the impingement device is configured to engage the outer surface of the tube and apply a force thereto in order to prevent the tube from sliding relative to the sheath seal when the impingement device is in a first state, and wherein the housing of the sheath seal further comprises one or more suture pads configured to permit passage of a suture therethrough to allow the sheath seal to be secured to a patient; and
   a y-connection, comprising a y-connection hub having a proximal end, a distal end, and a lumen arranged between the proximal end and the distal end of the y-connection hub, wherein the y-connection hub is connected to the housing of the sheath seal.

2. The balloon catheter assembly of claim 1, wherein the impingement device comprises a moveable pressure element disposed to exert pressure on the outer surface of the tube when the impingement device is in the first state in order to prevent the tube from sliding relative to the sheath seal, and wherein the pressure element is moveable to exert less pressure on the outer surface of the tube when the impingement device is in a second state so as to permit sliding of the tube relative to the sheath seal.

3. The balloon catheter assembly of claim 2, wherein the housing of the sheath seal further comprises a collapsible section arranged between the proximal end of the housing and the distal end of the housing, wherein the collapsible section is configured so that application of pressure to the collapsible section of the housing causes the impingement device to move from the first state to the second state.

4. The balloon catheter assembly of claim 2, wherein the moveable pressure element is selected from the group consisting of a static interference pinch lock, a bend disposed in the housing, an off axis center section disposed to impinge the tube in the first state, and an offset pinch that opens the lumen of the housing when pinched.

5. The balloon catheter assembly of claim 2, wherein the housing of the sheath seal comprises a plurality of tabs extending therefrom, and wherein application of pressure to the plurality of tabs moves the pressure element so the impingement device transitions to the second state.

6. The balloon catheter assembly of claim 1, wherein the distal end of the housing of the sheath seal is tapered.

7. The balloon catheter assembly of claim 1, wherein the elastomeric housing comprises a thermoplastic elastomer.

8. The balloon catheter assembly of claim 1, wherein between the proximal end of the y-connection hub and the distal end of the housing of the sheath seal there extends a lumen that is angled with respect to one or both of the lumen of the sheath seal and the lumen of the y-connection hub.

9. The balloon catheter assembly of claim 1, wherein the impingement device comprises a channel defined by one or more sidewalls disposed in the lumen of the sheath seal.

10. The balloon catheter assembly of claim 9, wherein a longitudinal axis defined by a center of the channel is offset from a longitudinal axis defined by a center of the lumen of the sheath seal.

11. The balloon catheter assembly of claim 1, wherein the distal end of the balloon catheter comprises a pre-formed curved portion.

12. The balloon catheter assembly of claim 11, wherein the pre-formed curved portion comprises a j-tip or a pigtail.

13. The balloon catheter assembly of claim 11, wherein the pre-formed curved portion comprises a j-tip, the j-tip comprising a first substantially straight segment connected to the distal end of the balloon catheter, a curved segment connected at a first end thereof to a distal end of the first substantially straight segment, and a second substantially straight segment attached to a second end of the curved segment, the second substantially straight segment arranged substantially parallel to the first substantially straight segment.

14. The balloon catheter assembly of claim 11, wherein the pre-formed curved portion comprises a j-tip, the j-tip comprising a thermoplastic.

15. The balloon catheter assembly of claim 14, wherein the thermoplastic comprises a thermoplastic polyurethane.

16. The balloon catheter assembly of claim 14, wherein the thermoplastic comprises a polyether-based thermoplastic polyurethane.

17. The balloon catheter assembly of claim 11, wherein the pre-formed curved portion comprises a j-tip, the j-tip comprising a metal.

18. The balloon catheter assembly of claim 11, wherein the pre-formed curved portion comprises a j-tip, wherein a diameter of a theoretical circle formed by the j-tip and the balloon catheter is greater than 8 mm.

19. The balloon catheter assembly of claim 1, wherein the distal end of the balloon catheter comprises an elongated extension.

20. The balloon catheter assembly of claim 1, wherein the at least one lumen of the tube comprises a sensor lumen, a gas lumen, and a guidewire lumen.

21. The balloon catheter assembly of claim 20, wherein the guidewire lumen is defined by a guidewire lumen sidewall comprising a polyimide tube.

22. The balloon catheter assembly of claim 21, wherein the polyimide tube is embedded in a sidewall of the balloon catheter, and the polyimide tube and the gas lumen are arranged in a co-lumen arrangement.

23. The balloon catheter assembly of claim 20, wherein the sensor lumen is defined by a sensor lumen sidewall and is arranged in a co-lumen arrangement with the gas lumen, and wherein the sensor lumen sidewall comprises one or more apertures in communication with an exterior of the balloon catheter.

24. The balloon catheter assembly of claim 23, wherein the guidewire lumen and the sensor lumen share a common sidewall.

25. The balloon catheter assembly of claim 20, wherein the sensor lumen, the gas lumen, and the guidewire lumen each have a cross-sectional diameter, and wherein the cross-sectional diameter of at least one of the sensor lumen, the gas lumen, and the guidewire lumen varies along a length of the balloon catheter.

26. The balloon catheter assembly of claim 1, wherein the balloon catheter has a length of approximately 18 inches or less.

27. A balloon catheter assembly comprising:
an intra-aortic balloon catheter comprising a proximal end, a distal end, and a tube arranged between the proximal end and the distal end, wherein the tube has an outer surface and an inner surface defining at least one lumen extending between the proximal end and the distal end, and a balloon membrane is disposed at the distal end, wherein the at least one lumen of the tube comprises a sensor lumen, a gas lumen, and a guidewire lumen;
a sheath seal comprising an elastomeric housing comprising a proximal end, a distal end, a lumen arranged between the proximal end of the housing and the distal end of the housing, wherein the housing comprises an impingement device, wherein the lumen of the sheath seal is configured to slidably receive the tube therein and the impingement device is configured to engage the outer surface of the tube and apply a force thereto in order to prevent the tube from sliding relative to the sheath seal when the impingement device is in a first state; and
a sensor disposed in the sensor lumen, wherein the sensor is disposed in a gap in the sensor lumen between two segments of a cured adhesive.

28. The balloon catheter assembly of claim 27, wherein the sensor comprises a sensing portion embedded in a silicone gel.

29. The balloon catheter assembly of claim 27, wherein the sensor is disposed at the distal end of the balloon catheter, proximal of the balloon membrane.

* * * * *